US012644857B2

(12) United States Patent
    Watanabe

(10) Patent No.:    US 12,644,857 B2
(45) Date of Patent:        Jun. 2, 2026

(54) CONTROL METHOD OF GAS SENSOR

(71) Applicant: NGK INSULATORS, LTD., Nagoya (JP)

(72) Inventor: Yusuke Watanabe, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 541 days.

(21) Appl. No.: 17/702,014

(22) Filed: Mar. 23, 2022

(65) Prior Publication Data

US 2022/0308007 A1     Sep. 29, 2022

(30) Foreign Application Priority Data

Mar. 29, 2021   (JP) ................................. 2021-056018
Feb. 22, 2022   (JP) ................................. 2022-025751

(51) Int. Cl.
G01N 27/406          (2006.01)
G01N 27/407          (2006.01)
        (Continued)

(52) U.S. Cl.
CPC ..... G01N 27/4067 (2013.01); G01N 27/4071 (2013.01); G01N 27/41 (2013.01); G01N 33/0037 (2013.01)

(58) Field of Classification Search
CPC ........... G01N 33/0037; G01N 27/4074; G01N 27/419; G01N 27/067; G01N 27/4071; G01N 27/41; Y02A 50/20
See application file for complete search history.

(56) References Cited

U.S. PATENT DOCUMENTS

2009/0051373 A1*   2/2009   Kato .................. G01N 27/4067
                                                            324/693
2012/0199478 A1    8/2012   Sasaki
                            (Continued)

FOREIGN PATENT DOCUMENTS

DE      10 2012 201 587 A1    8/2012
DE      11 2021 000 184 T5    9/2022
                            (Continued)

OTHER PUBLICATIONS

Unexamined U.S. Appl. No. 17/702,005, filed Mar. 23, 2022.
                            (Continued)

*Primary Examiner* — Luan V Van
*Assistant Examiner* — Randall Lee Gamble, Jr.
(74) *Attorney, Agent, or Firm* — MATTINGLY & MALUR, PC

(57)                    ABSTRACT
A control method of a gas sensor including a sensor element and an activity determining part includes a temperature raising step of heating the sensor element by a heater of the sensor element to raise a temperature of the sensor element up to an active temperature at which the activity determining part determines that the sensor element is in a measurable active state; a prior driving step of raising the temperature of the sensor element by the heater from the active temperature up to a steady driving temperature, and operating a main pump cell and a measurement pump cell of the sensor element to detect NOx in the measurement-object gas; and a steady driving step of maintaining the temperature of the sensor element by the heater at the steady driving temperature, and operating the main pump cell and the measurement pump cell to continuously detect NOx in the measurement-object gas.

13 Claims, 6 Drawing Sheets

(51) Int. Cl.
    _G01N 27/41_          (2006.01)
    _G01N 33/00_          (2006.01)

(56)                    References Cited

U.S. PATENT DOCUMENTS

| | | | |
|---|---|---|---|
| 2015/0268192 A1 | 9/2015 | Saito et al. | |
| 2018/0100828 A1* | 4/2018 | Okamoto | G01N 27/419 |
| 2019/0383766 A1* | 12/2019 | Nakagaki | G01N 27/4067 |
| 2022/0283114 A1 | 9/2022 | Okamoto et al. | |

FOREIGN PATENT DOCUMENTS

| | | | | |
|---|---|---|---|---|
| JP | 2006214885 A | * | 8/2006 | |
| JP | 2009-69140 A | | 4/2009 | |
| JP | 2009145235 A | * | 7/2009 | |
| JP | 2015-184109 A | | 10/2015 | |
| JP | 6208060 B2 | | 10/2017 | |

OTHER PUBLICATIONS

Unexamined U.S. Appl. No. 17/702,018, filed Mar. 23, 2022.
Japanese Office Action received in corresponding Japanese Application No. 2022-025751 dated Jun. 24, 2025.
German Office Action received in corresponding German Application No. 10 2022 106 151.5 dated Dec. 2, 2024.

* cited by examiner

Fig. 1

CONTROL METHOD OF GAS SENSOR

CROSS-REFERENCE TO RELATED APPLICATION

The present application claims priority from Japanese applications JP2021-056018, filed on Mar. 29, 2021 and JP2022-025751, filed Feb. 22, 2022, the contents of which are hereby incorporated by reference into this application.

BACKGROUND OF THE INVENTION

Technical Field of the Invention

The present invention relates to a control method of a gas sensor.

Background Art

A gas sensor is used for detection or measurement of concentration of an objective gas component (oxygen $O_2$, nitrogen oxide NOx, ammonia $NH_3$, hydrocarbon HC, carbon dioxide $CO_2$, etc.) in a measurement-object gas, such as exhaust gas of automobile. For example, conventionally, the concentration of the objective gas component in exhaust gas of an automobile is measured, and an exhaust gas cleaning system mounted on the automobile is optimally controlled based on the measurement.

As such a gas sensor, a gas sensor equipped with a sensor element using an oxygen ion conductive solid electrolyte such as zirconia ($ZrO_2$) is known. In order to detect an objective gas component, the gas sensor is used in the state of a sensor element being heated up to a temperature at which the oxygen-ion-conductivity of a solid electrolyte is developed.

For example, JP6208060B2 discloses that a sensor element provided in a gas sensor includes a heater for heating the sensor element. Further, JP6208060B2 discloses, as a sensor element, an embodiment comprising a main pump cell and an auxiliary pump cell for adjusting an oxygen concentration and a measuring pumping cell for detecting a gas component to be measured (e.g., NOx).

Further, JP6208060B2 discloses a method for setting a temperature rising profile for raising the temperature of a sensor element up to a predetermined operating temperature and an example of the temperature rising profile (FIG. 7).

CITATION LIST

Patent Document

Patent Document 1: JP6208060B2

SUMMARY OF THE INVENTION

Problems to be Solved by the Invention

A gas sensor is used for control of an exhaust gas purification system or the like installed in an automobile, and is required to accurately measure the concentration of a target gas to be measured (e.g., oxygen $O_2$, nitrogen oxides NOx, ammonia $NH_3$, hydrocarbons HC, carbon dioxide $CO_2$). The gas sensor is also required to start accurate measurement in a short time as much as possible after its start-up.

In the gas sensor, a sensor element needs to be heated up to a temperature at which the oxygen-ion-conductivity of a solid electrolyte is developed. Therefore, the time from when the gas sensor receives a start signal (Dew point) from the exhaust gas purification system or the like until when accurate measurement can be started (i.e., a start-up time) mainly depends on the time required to heat the sensor element.

During the start-up time of the gas sensor, the target gas to be measured (e.g., nitrogen oxides NOx) cannot be detected, and therefore the exhaust gas purification system does not satisfactorily function so that nitrogen oxides NOx or the like contained in exhaust gas may directly be discharged without being purified. In order to reduce the occurrence of such a situation, the start-up time is required to be reduced.

Further, when NOx and a high concentration of oxygen are present in a measurement-object gas, it generally tends to be difficult to maintain high measurement accuracy of a NOx concentration.

It is therefore an object of the present invention to provide a method for controlling a gas sensor at the time of start-up, which makes it possible to reduce a start-up time from when the gas sensor starts up until when accurate measurement can be started.

It is also an object of the present invention to provide a method for controlling a gas sensor at the time of start-up, which makes it possible to achieve a short start-up time from when the gas sensor starts up until when accurate measurement can be started and to maintain high NOx detection accuracy of the gas sensor during long-time use even when the oxygen concentration in a measurement-object gas is high.

Means for Solving the Problems

In order to reduce the start-up time, the present inventor has studied a reduction of the time required to heat the sensor element up to a desired temperature (i.e., a heating-up time) as follows.

In order to reduce the heating-up time, the temperature-rising-rate of a heater may be increased. However, it has been confirmed that there is a problem that an excessively high temperature-rising-rate of the heater causes an increased risk of occurrence of cracks in the internal structure of the sensor element. This will be described later in detail in Comparative Embodiment 1.

On the other hand, the risk of occurrence of cracks in the internal structure of the sensor element can be reduced by reducing the temperature-raising-rate as the temperature of the sensor element increases in accordance with the temperature rising profile disclosed in JP6208060B2. However, the temperature-raising-rate in a range where the temperature of the sensor element is high (in a range close to a driving temperature) needs to be reduced, which tends to increase the heating-up time.

Alternatively, in order to reduce the heating-up time, the driving temperature of the sensor element may be reduced. However, if the driving temperature is too low, the oxygen-ion-conductivity of a solid electrolyte constituting the sensor element decreases. As a result, it has been confirmed that there is a problem that the target gas to be measured (e.g., nitrogen oxides NOx) cannot be accurately detected particularly when the oxygen concentration in the measurement-object gas is high. This will be described later in detail in Comparative Embodiment 2.

As a result of intensive studies, the present inventor has found that the start-up time from when the gas sensor starts up until when measurement can be started can be reduced by controlling the gas sensor in such a manner that an activity determining part of the gas sensor determines whether the sensor element is in a measurable active state or not, prior driving is started at a heater temperature at which the sensor element is determined to be in a measurable active state (i.e., at an active temperature), and then steady driving is performed after a steady driving temperature is reached. Further, the present inventor has also found that control of the gas sensor by such a control method makes it possible to maintain high NOx detection accuracy of the gas sensor during long-term use even when the oxygen concentration in the measurement-object gas is high.

The present invention includes the following aspects.

(1) A control method of a gas sensor for detecting NOx in a measurement-object gas, the gas sensor comprising:

a sensor element, and an activity determining part for determining whether the sensor element is in a measurable active state or not, wherein the sensor element comprises:

a base part in an elongated plate shape, including a plurality of oxygen-ion-conductive solid electrolyte layers stacked;

a measurement-object gas flow part for introduction and flow of a measurement-object gas through one end part in a longitudinal direction of the base part;

a main pump cell for adjusting an oxygen concentration in the measurement-object gas to a desired concentration, the main pump cell including: an inner main pump electrode disposed on an inner surface of the measurement-object gas flow part; and an outer pump electrode disposed at a position different from the measurement-object gas flow part on the base part and corresponding to the inner main pump electrode;

a measurement pump cell for detecting NOx in the measurement-object gas, the measurement pump cell including: a measurement electrode disposed at a position farther from the one end part in the longitudinal direction of the base part than the inner main pump electrode on the inner surface of the measurement-object gas flow part; and an outer pump electrode disposed at a position different from the measurement-object gas flow part on the base part and corresponding to the measurement electrode;

a heater for heating the base part; and a reference electrode disposed inside the base part to be in contact with a reference gas, and the control method comprising:

a temperature raising step of heating the sensor element by the heater to raise a temperature of the sensor element up to an active temperature at which the activity determining part determines that the sensor element is in a measurable active state;

a prior driving step of raising the temperature of the sensor element by the heater from the active temperature up to a steady driving temperature, and operating the main pump cell and the measurement pump cell to detect NOx in the measurement-object gas; and a steady driving step of maintaining the temperature of the sensor element by the heater at the steady driving temperature, and operating the main pump cell and the measurement pump cell to continuously detect NOx in the measurement-object gas.

(2) The control method according to the above (1), wherein an oxygen concentration adjusted by the main pump cell in the prior driving step is higher than an oxygen concentration adjusted by the main pump cell in the steady driving step.

4

(3) The control method according to the above (1) or (2), wherein the sensor element further comprises:

an auxiliary pump cell including an auxiliary pump electrode disposed at a position farther from the one end part in the longitudinal direction of the base part than the inner main pump electrode on the inner surface of the measurement-object gas flow part, and an outer pump electrode disposed at a position different from the measurement-object gas flow part on the base part and corresponding to the auxiliary pump electrode, wherein the auxiliary pump electrode is disposed at a position closer to the one end part in the longitudinal direction of the base part than the measurement electrode.

(4) The control method according to the above (3), wherein, in the auxiliary pump cell, a pump current flowing through the auxiliary pump cell is controlled based on an electromotive force between the auxiliary pump electrode and the reference electrode; and in the main pump cell, an electromotive force between the inner main pump electrode and the reference electrode is controlled so that the pump current flowing through the auxiliary pump cell is at a constant value.

(5) The control method according to the above (4), wherein, in the prior driving step, an electromotive force between the auxiliary pump electrode and the reference electrode is controlled to a smaller value than an electromotive force between the auxiliary pump electrode and the reference electrode in the steady driving step.

(6) The control method according to the above (4) or (5), wherein, in the prior driving step, a pump current flowing through the auxiliary pump cell is controlled to a larger value than a pump current flowing through the auxiliary pump cell in the steady driving step.

(7) The control method according to any one of the above (1) to (6), wherein, in the measurement pump cell, a pump current flowing through the measurement pump cell is controlled based on an electromotive force between the measurement electrode and the reference electrode; and in the prior driving step, an electromotive force between the measurement electrode and the reference electrode is controlled to a different value from an electromotive force between the measurement electrode and the reference electrode in the steady driving step.

(8) The control method according to the above (7), wherein, in the prior driving step, an electromotive force between the measurement electrode and the reference electrode is controlled to a larger value than an electromotive force between the measurement electrode and the reference electrode in the steady driving step.

(9) The control method according to any one of the above (1) to (8), wherein the activity determining part determines whether the sensor element is in a measurable active state or not, based on at least one selected from the group consisting of a temperature of the heater, a resistance value of the main pump cell, and a resistance value between the inner main pump electrode and the reference electrode.

(10) The control method according to any one of the above (1) to (9), wherein, in the prior driving step, the heater is heated from the active temperature up to the steady driving temperature based on a predetermined temperature-raising-rate in the prior driving step.

(11) The control method according to the above (10), wherein the temperature-raising-rate in the prior driving step is set in multi stages.

(12) The control method according to any one of the above (1) to (11), wherein, in the temperature raising step, the heater is heated up to the active temperature based on a predetermined temperature-raising-rate in the temperature raising step.

(13) The control method according to the above (12), wherein the temperature-raising-rate in the temperature raising step is set in multi stages.

(14) A gas sensor comprising a sensor element and a control unit for controlling the sensor element, wherein the sensor element comprises:

a base part in an elongated plate shape, including a plurality of oxygen-ion-conductive solid electrolyte layers stacked;

a measurement-object gas flow part for introduction and flow of a measurement-object gas through one end part in a longitudinal direction of the base part;

a main pump cell for adjusting an oxygen concentration in the measurement-object gas to a desired concentration, the main pump cell including: an inner main pump electrode disposed on an inner surface of the measurement-object gas flow part; and an outer pump electrode disposed at a position different from the measurement-object gas flow part on the base part and corresponding to the inner main pump electrode;

a measurement pump cell for detecting NOx in the measurement-object gas, the measurement pump cell including: a measurement electrode disposed at a position farther from the one end part in the longitudinal direction of the base part than the inner main pump electrode on the inner surface of the measurement-object gas flow part; and an outer pump electrode disposed at a position different from the measurement-object gas flow part on the base part and corresponding to the measurement electrode;

a heater for heating the base part; and a reference electrode disposed inside the base part to be in contact with a reference gas, and the control unit comprises:

an activity determining part for determining whether the sensor element is in a measurable active state or not;

a heater control part for controlling a temperature of the heater; and a pump control part for operating the main pump cell and the measurement pump cell to detect NOx in the measurement-object gas, wherein the activity determining part determines whether the sensor element is in a measurable active state or not;

the heater control part heats the sensor element by the heater up to an active temperature at which the activity determining part determines that the sensor element is in a measurable active state, and further heats the sensor element up to a steady driving temperature; and the pump control part starts to operate the main pump cell and the measurement pump cell when the sensor element reaches the active temperature, and further continues to operate the main pump cell and the measurement pump cell when the sensor element reaches the steady driving temperature.

According to the present invention, it is possible to reduce a start-up time from when the gas sensor starts up until when accurate measurement can be started.

Further, according to the present invention, it is possible to achieve a short start-up time from when the gas sensor starts up until when accurate measurement can be started and to maintain high NOx detection accuracy of the gas sensor during long-time use even when the oxygen concentration in a measurement-object gas is high.

BRIEF DESCRIPTION OF THE DRAWINGS

FIG. 1 is a vertical sectional schematic view in a longitudinal direction, showing one example of a general configuration of a gas sensor 100.

MODES FOR CARRYING OUT OF THE INVENTION

A gas sensor of the present invention includes a sensor element for controlling the sensor element.

The sensor element of the present invention includes:

a base part in an elongated plate shape, including a plurality of oxygen-ion-conductive solid electrolyte layers stacked;

a measurement-object gas flow part for introduction and flow of a measurement-object gas through one end part in a longitudinal direction of the base part;

a main pump cell for adjusting an oxygen concentration in the measurement-object gas to a desired concentration, the main pump cell including: an inner main pump electrode disposed on an inner surface of the measurement-object gas flow part; and an outer pump electrode disposed at a position different from the measurement-object gas flow part on the base part and corresponding to the inner main pump electrode;

a measurement pump cell for detecting NOx in the measurement-object gas, the measurement pump cell including: a measurement electrode disposed at a position farther from the one end part in the longitudinal direction of the base part than the inner main pump electrode on the inner surface of the measurement-object gas flow part; and an outer pump electrode disposed at a position different from the measurement-object gas flow part on the base part and corresponding to the measurement electrode;

a heater for heating the base part; and a reference electrode disposed inside the base part to be in contact with a reference gas.

The control unit of the present invention includes:

an activity determining part for determining whether the sensor element is in a measurable active state or not;

a heater control part for controlling a temperature of the heater; and a pump control part for operating the main pump cell and the measurement pump cell to detect NOx in the measurement-object gas.

Hereinafter, an example of an embodiment of the gas sensor of the present invention will be described in detail.

[General Configuration of Gas Sensor]

Figure 1:
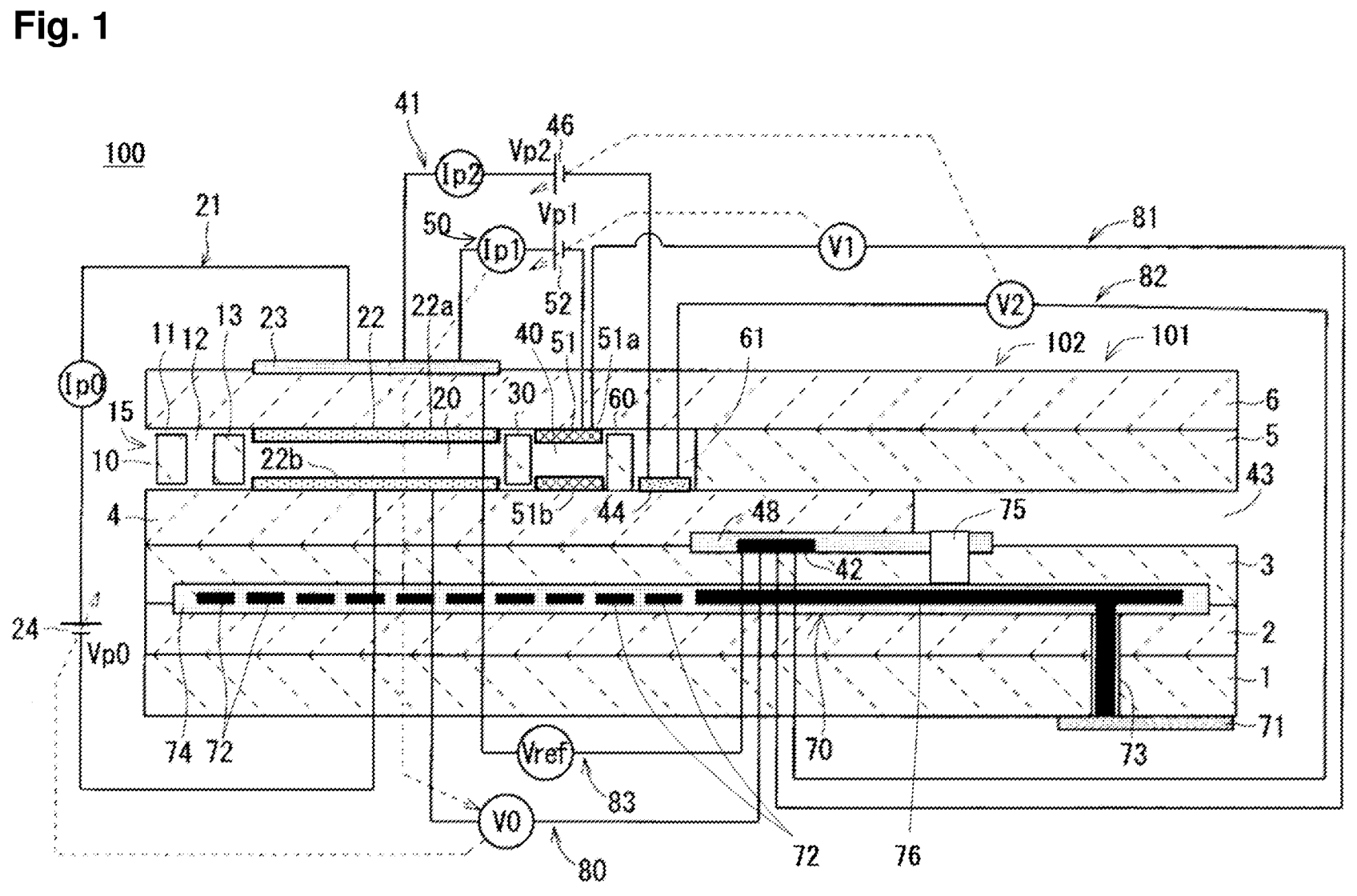

The sensor element of the present invention will now be described with reference to the drawings. FIG. 1 is a vertical sectional schematic view in the longitudinal direction, showing one example of a general configuration of a gas sensor 100 including a sensor element 101. Hereinafter, based on FIG. 1, the upper side and the lower side in FIG. 1 are respectively defined as top and bottom, and the left side and the right side in FIG. 1 are respectively defined as a front end side and a rear end side.

In FIG. 1, the gas sensor 100 represents one example of a limiting current type NOx sensor that detects NOx in a measurement-object gas by the sensor element 101, and measures the concentration of NOx.

Figure 2:
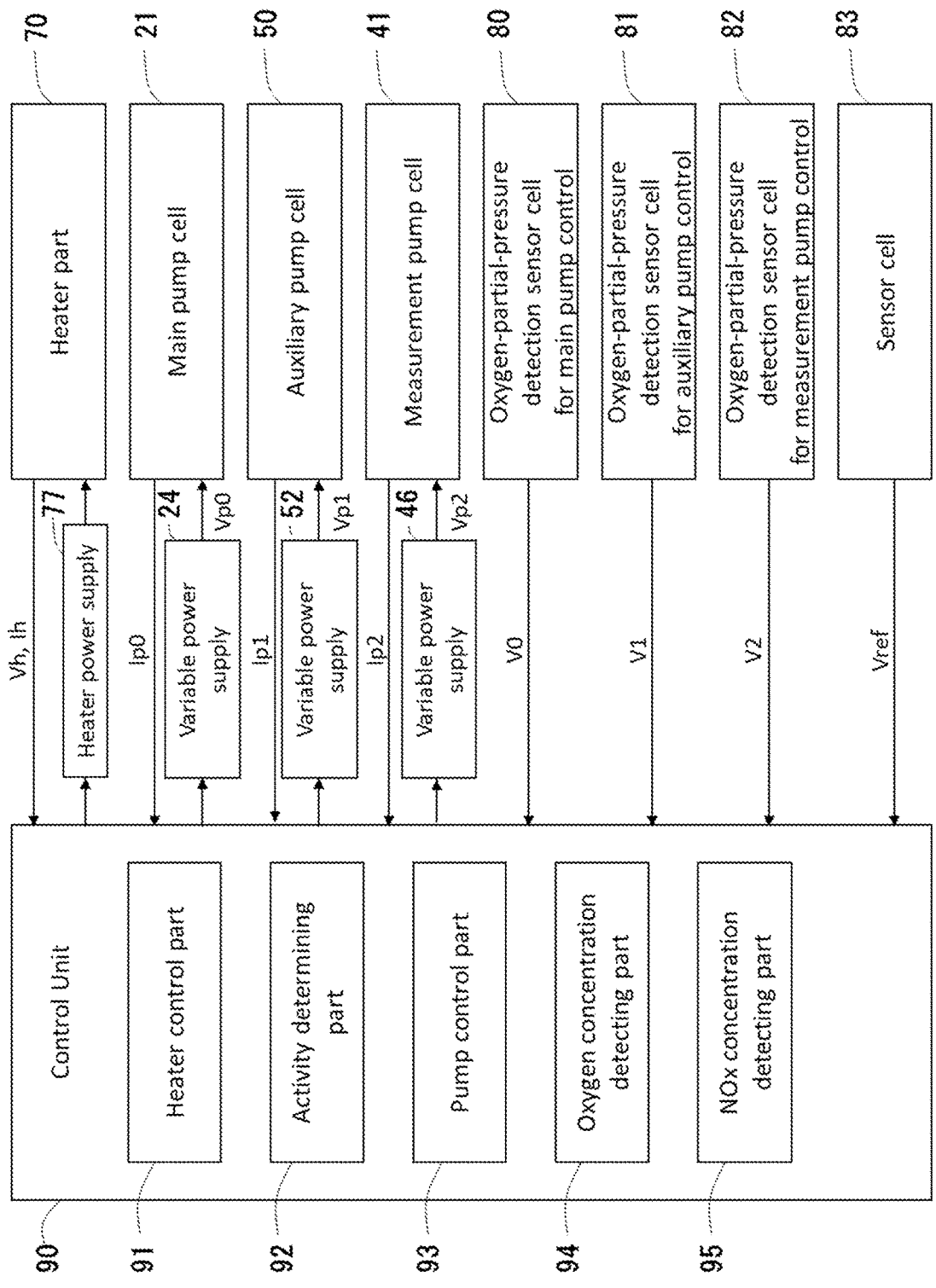
FIG. 2 is a block diagram showing connections between a control unit 90, and individual pump cells 21, 50, and 41 and a heater part 70 of a sensor element 101.

Further, the gas sensor 100 includes a control unit 90. FIG. 2 is a block diagram showing connections between the control unit 90 and the sensor element 101.

(Sensor Element)

The sensor element 101 is an element in an elongated plate shape, including a base part 102 having such a structure that a plurality of oxygen-ion-conductive solid electrolyte layers are layered. The elongated plate shape also called a long plate shape or a belt shape. The base part 102 has such a structure that six layers, namely, a first substrate layer 1, a second substrate layer 2, a third substrate layer 3, a first solid electrolyte layer 4, a spacer layer 5, and a second solid electrolyte layer 6, are layered in this order from the bottom side, as viewed in the drawing. Each of the six layers is formed of an oxygen-ion-conductive solid electrolyte layer containing, for example, zirconia ($ZrO_2$). The solid electrolyte forming these six layers is dense and gastight. These six layers all may have the same thickness, or the thickness may vary among the layers. The layers are adhered to each other with an adhesive layer of a solid electrolyte interposed therebetween, and the base part 102 includes the adhesive layer. While a layer configuration composed of the six layers is illustrated in FIG. 1, the layer configuration in the present invention is not limited to this, and any number of layers and any layer configuration are possible.

The sensor element 101 is manufactured, for example, by stacking ceramic green sheets corresponding to the individual layers after conducting predetermined processing, printing of circuit pattern and the like, and then firing the stacked ceramic green sheets so that they are combined together.

A gas inlet 10 is formed between the lower surface of the second solid electrolyte layer 6 and the upper surface of the first solid electrolyte layer 4 in one end part in the longitudinal direction (hereinafter, referred to as a front end part) of the sensor element 101. A measurement-object gas flow part 15 is formed in such a form that a first diffusion-rate limiting part 11, a buffer space 12, a second diffusion-rate limiting part 13, a first internal cavity 20, a third diffusion-rate limiting part 30, a second internal cavity 40, a fourth diffusion-rate limiting part 60, and a third internal cavity 61 communicate in this order in the longitudinal direction from the gas inlet 10.

The gas inlet 10, the buffer space 12, the first internal cavity 20, the second internal cavity 40, and the third internal cavity 61 constitute an internal space of the sensor element 101. The internal space is provided in such a manner that a portion of the spacer layer 5 is hollowed out, and the top of the internal space is defined by the lower surface of the second solid electrolyte layer 6, the bottom of the internal space is defined by the upper surface of the first solid electrolyte layer 4, and the lateral surface of the internal space is defined by the lateral surface of the spacer layer 5.

Each of the first diffusion-rate limiting part 11, the second diffusion-rate limiting part 13, and the third diffusion-rate limiting part 30 is provided as two laterally elongated slits (having the longitudinal direction of the openings in the direction perpendicular to the figure in FIG. 1). Each of the first diffusion-rate limiting part 11, the second diffusion-rate limiting part 13, and the third diffusion-rate limiting part 30 may be in such a form that a desired diffusion resistance is created, but the form is not limited to the slits.

The fourth diffusion-rate limiting part 60 is provided as a single laterally elongated slit (having the longitudinal direction of the opening in the direction perpendicular to the figure in FIG. 1) between the spacer layer 5 and the second solid electrolyte layer 6. The fourth diffusion-rate limiting part 60 may be in such a form that a desired diffusion resistance is created, but the form is not limited to the slits.

Also, at a position farther from the front end than the measurement-object gas flow part 15, a reference gas introduction space 43 is disposed between the upper surface of the third substrate layer 3 and the lower surface of the spacer layer 5 at a position where the reference gas introduction space 43 is laterally defined by the lateral surface of the first solid electrolyte layer 4. The reference gas introduction space 43 has an opening in the other end part (hereinafter, referred to as a rear end part) of the sensor element 101. As a reference gas for NOx concentration measurement, for example, air is introduced into the reference gas introduction space 43.

An air introduction layer 48 is a layer formed of porous alumina, and is so configured that a reference gas is introduced into the air introduction layer 48 via the reference gas introduction space 43. The air introduction layer 48 is formed to cover a reference electrode 42.

The reference electrode 42 is an electrode sandwiched between the upper surface of the third substrate layer 3 and the first solid electrolyte layer 4, and as described above, the air introduction layer 48 leading to the reference gas introduction space 43 is disposed around the reference electrode 42. That is, the reference electrode 42 is disposed to be in contact with a reference gas via the air introduction layer 48 which is a porous material, and the reference gas introduction space 43. As will be described later, the reference electrode 42 can be used to measure the oxygen concentration (oxygen partial pressure) in the first internal cavity 20, the second internal cavity 40, and the third internal cavity 61.

In the measurement-object gas flow part 15, the gas inlet 10 is open to the external space, and the measurement-object gas is taken into the sensor element 101 from the external space through the gas inlet 10.

In the present embodiment, the measurement-object gas flow part 15 is in such a form that the measurement-object gas is introduced through the gas inlet 10 that is open on the front end surface of the sensor element 101, however, the present invention is not limited to this form. For example, the measurement-object gas flow part 15 need not have a recess of the gas inlet 10. In this case, the first diffusion-rate limiting part 11 substantially serves as a gas inlet.

For example, the measurement-object gas flow part 15 may have an opening that communicates with the buffer space 12 or a position near the buffer space 12 of the first internal cavity 20, on a lateral surface along the longitudinal direction of the base part 102. In this case, the measurement-object gas is introduced from the lateral surface along the longitudinal direction of the base part 102 through the opening.

Further, for example, the measurement-object gas flow part 15 may be so configured that the measurement-object gas is introduced through a porous body.

The first diffusion-rate limiting part 11 creates a predetermined diffusion resistance to the measurement-object gas taken through the gas inlet 10.

The buffer space 12 is provided to guide the measurement-object gas introduced from the first diffusion-rate limiting part 11 to the second diffusion-rate limiting part 13.

The second diffusion-rate limiting part 13 creates a predetermined diffusion resistance to the measurement-object gas introduced into the first internal cavity 20 from the buffer space 12.

It suffices that the amount of the measurement-object gas to be introduced into the first internal cavity 20 falls within a predetermined range. That is, it suffices that a predetermined diffusion resistance is created in a whole from the front end part of the sensor element 101 to the second diffusion-rate limiting part 13. For example, the first diffusion-rate limiting part 11 may directly communicate with the first internal cavity 20, or the buffer space 12 and the second diffusion-rate limiting part 13 may be absent.

The buffer space 12 is provided to mitigate the influence of pressure fluctuation on the detected value when the pressure of the measurement-object gas fluctuates.

When the measurement-object gas is introduced from outside the sensor element 101 into the first internal cavity 20, the measurement-object gas, which is rapidly taken through the gas inlet 10 into the sensor element 101 due to pressure fluctuation of the measurement-object gas in the external space (pulsations in exhaust pressure if the measurement-object gas is automotive exhaust gas), is not directly introduced into the first internal cavity 20. Rather, the measurement-object gas is introduced into the first internal cavity 20 after the pressure fluctuation of the measurement-object gas is eliminated through the first diffusion-rate limiting part 11, the buffer space 12, and the second diffusion-rate limiting part 13. Thus, the pressure fluctuation of the measurement-object gas introduced into the first internal cavity 20 becomes almost negligible.

The first internal cavity 20 is provided as a space for adjusting the oxygen partial pressure in the measurement-object gas introduced through the second diffusion-rate limiting part 13. The oxygen partial pressure is adjusted by operation of a main pump cell 21.

The main pump cell 21 is an electrochemical pump cell including an inner main pump electrode 22 disposed on an inner surface of the measurement-object gas flow part 15, and an outer pump electrode 23 disposed at a position different from the measurement-object gas flow part 15 on the base part 102 (in FIG. 1, on an outer surface of the base part 102) and corresponding to the inner main pump electrode 22. The phrase "corresponding to the inner main pump electrode 22" means that the outer pump electrode 23 and the inner main pump electrode 22 are provided with the second solid electrolyte layer 6 being interposed therebetween.

That is, the main pump cell 21 is an electrochemical pump cell composed of the inner main pump electrode 22 having a ceiling electrode portion 22a disposed over substantially the entire surface of the lower surface of the second solid electrolyte layer 6 that faces the first internal cavity 20, the outer pump electrode 23 disposed on a region of the upper surface of the second solid electrolyte layer 6 that corresponds to the ceiling electrode portion 22a so as to be exposed to the external space, and the second solid electrolyte layer 6 sandwiched between the inner main pump electrode 22 and the outer pump electrode 23.

The inner main pump electrode 22 is formed to span the upper and lower solid electrolyte layers (the second solid electrolyte layer 6 and the first solid electrolyte layer 4) that define the first internal cavity 20 and the spacer layer 5 that defines the lateral wall. Specifically, the ceiling electrode portion 22a is formed on the lower surface of the second solid electrolyte layer 6 that defines the ceiling surface of the first internal cavity 20, and a bottom electrode portion 22b is formed on the upper surface of the first solid electrolyte layer 4 that defines the bottom surface of the first internal cavity 20. Also, lateral electrode portions (not shown) are formed on the lateral wall surfaces (inner surface) of the spacer layer 5 that form both lateral wall parts of the first internal cavity 20 so as to connect the ceiling electrode portion 22a and the bottom electrode portion 22b. Thus, the inner main pump electrode 22 is provided as a tunnel-like structure in the area where the lateral electrode portions are disposed.

The inner main pump electrode 22 and the outer pump electrode 23 are each formed as a porous cermet electrode (e.g., a cermet electrode of Pt containing 1% Au and $ZrO_2$). It is to be noted that the inner main pump electrode 22 to be in contact with the measurement-object gas is formed using a material having a weakened ability to reduce a NOx component in the measurement-object gas.

In the main pump cell 21, a desired pump voltage Vp0 is applied between the inner main pump electrode 22 and the outer pump electrode 23 by a variable power supply 24 to flow a pump current Ip0 between the inner main pump electrode 22 and the outer pump electrode 23 in either a positive or negative direction, and thus it is possible to pump out oxygen in the first internal cavity 20 to the external space or pump oxygen into the first internal cavity 20 from the external space.

To detect the oxygen concentration (oxygen partial pressure) in the atmosphere in the first internal cavity 20, the inner main pump electrode 22, the second solid electrolyte layer 6, the spacer layer 5, the first solid electrolyte layer 4, the third substrate layer 3, and the reference electrode 42 form an electrochemical sensor cell, namely, an oxygen-partial-pressure detection sensor cell 80 for main pump control.

The oxygen concentration (oxygen partial pressure) in the first internal cavity 20 can be detected from an electromotive force V0 measured in the oxygen-partial-pressure detection sensor cell 80 for main pump control. In addition, the pump current Ip0 is controlled by performing feedback control of the pump voltage Vp0 so that the electromotive force V0 is constant. Thus, the oxygen concentration in the first internal cavity 20 can be maintained at a predetermined constant value.

The third diffusion-rate limiting part 30 creates a predetermined diffusion resistance to the measurement-object gas whose oxygen concentration (oxygen partial pressure) has been controlled in the first internal cavity 20 by the operation of the main pump cell 21 and guides the measurement-object gas into the second internal cavity 40.

The second internal cavity 40 is provided as a space for adjusting the oxygen partial pressure in the measurement-object gas introduced through the third diffusion-rate limiting part 30 more accurately. The oxygen partial pressure is adjusted by operation of an auxiliary pump cell 50. The sensor element 101 may be configured without the second internal cavity 40 and the auxiliary pump cell 50. From the viewpoint of adjusting accuracy of oxygen partial pressure, it is more preferred that the second internal cavity 40 and the auxiliary pump cell 50 be provided.

After the oxygen concentration (oxygen partial pressure) in the measurement-object gas is adjusted in advance in the first internal cavity 20, the measurement-object gas is introduced through the third diffusion-rate limiting part 30, and is further subjected to adjustment of the oxygen partial pressure by the auxiliary pump cell 50 in the second internal cavity 40. Thus, the oxygen concentration in the second internal cavity 40 can be kept constant with high accuracy, and the NOx concentration can be measured with high accuracy in the gas sensor 100.

The auxiliary pump cell 50 is an electrochemical pump cell including an auxiliary pump electrode 51 disposed at a position farther from the front end portion in the longitudinal direction of the base part 102 than the inner main pump electrode 22 on the inner surface of the measurement-object gas flow part 15, and the outer pump electrode 23 disposed at a position different from the measurement-object gas flow part 15 on the base part 102 (in FIG. 1, on the outer surface of the base part 102) and corresponding to the auxiliary pump electrode 51. The phrase "corresponding to the auxiliary pump electrode 51" means that the outer pump electrode 23 and the auxiliary pump electrode 51 are provided with the second solid electrolyte layer 6 being interposed therebetween.

That is, the auxiliary pump cell 50 is an auxiliary electrochemical pump cell composed of the auxiliary pump electrode 51 having a ceiling electrode portion 51a disposed on substantially the entire surface of lower surface of the second solid electrolyte layer 6 facing with the second internal cavity 40, the outer pump electrode 23 (the outer electrode is not limited to the outer pump electrode 23, but may be any suitable electrode outside the sensor element 101), and the second solid electrolyte layer 6.

This auxiliary pump electrode 51 is disposed in the second internal cavity 40 in a tunnel-like structure similar to the inner main pump electrode 22 disposed in the first internal cavity 20 described previously. Specifically, in the tunnel-like structure, the ceiling electrode portion 51a is formed on the lower surface of the second solid electrolyte layer 6 that defines the ceiling surface of the second internal cavity 40, a bottom electrode portion 51b is formed on the upper surface of the first solid electrolyte layer 4 that defines the bottom surface of the second internal cavity 40, and lateral electrode portions (not shown) connecting the ceiling electrode portion 51a and the bottom electrode portion 51b are formed on the wall surfaces of the spacer layer 5 that define the lateral walls of the second internal cavity 40.

It is to be noted that the auxiliary pump electrode 51 is formed using a material having a weakened ability to reduce a NOx component in the measurement-object gas, as with the case of the inner main pump electrode 22.

In the auxiliary pump cell 50, by applying a desired voltage Vp1 between the auxiliary pump electrode 51 and the outer pump electrode 23 by a variable power supply 52, it is possible to pump out oxygen in the atmosphere in the second internal cavity 40 to the external space, or pump the oxygen into the second internal cavity 40 from the external space.

To control the oxygen partial pressure in the atmosphere in the second internal cavity 40, the auxiliary pump electrode 51, the reference electrode 42, the second solid electrolyte layer 6, the spacer layer 5, the first solid electrolyte layer 4, and the third substrate layer 3 constitute an electrochemical sensor cell, namely, an oxygen-partial-pressure detection sensor cell 81 for auxiliary pump control.

The auxiliary pump cell 50 performs pumping with the variable power supply 52 whose voltage is controlled on the basis of an electromotive force V1 detected by the oxygen-partial-pressure detection sensor cell 81 for auxiliary pump control. Thus, the oxygen partial pressure in the atmosphere in the second internal cavity 40 is controlled to such a low partial pressure that does not substantially affect measurement of NOx.

In addition, a pump current Ip1 is used for control of the electromotive force V0 of the oxygen-partial-pressure detection sensor cell 80 for main pump control. Specifically, the pump current Ip1 is input to the oxygen-partial-pressure detection sensor cell 80 for main pump control as a control signal to control the electromotive force V0, and thus the gradient of the oxygen partial pressure in the measurement-object gas introduced into the second internal cavity 40 from the third diffusion-rate limiting part 30 is controlled to remain constant. In using as a NOx sensor, the oxygen concentration in the second internal cavity 40 is kept at a constant value of about 0.001 ppm by the actions of the main pump cell 21 and the auxiliary pump cell 50.

The fourth diffusion-rate limiting part 60 creates a predetermined diffusion resistance to the measurement-object gas whose oxygen concentration (oxygen partial pressure) has been controlled to further low in the second internal cavity 40 by the operation of the auxiliary pump cell 50, and guides the measurement-object gas into the third internal cavity 61.

The third internal cavity 61 is provided as a space for measuring nitrogen oxide (NOx) concentration in the measurement-object gas introduced through the fourth diffusion-rate limiting part 60. By the operation of a measurement pump cell 41, NOx concentration is measured.

The measurement pump cell 41 is an electrochemical pump cell including a measurement electrode 44 disposed at a position farther from the front end portion in the longitudinal direction of the base part 102 than the auxiliary pump electrode 51 on the inner surface of the measurement-object gas flow part 15, and the outer pump electrode 23 disposed at a position different from the measurement-object gas flow part 15 on the base part 102 (in FIG. 1, on the outer surface of the base part 102) and corresponding to the measurement electrode 44. The phrase "corresponding to the measurement electrode 44" means that the outer pump electrode 23 and the measurement electrode 44 are provided with the second solid electrolyte layer 6, the spacer layer 5, and the first solid electrolyte layer 4 being interposed therebetween.

That is, the measurement pump cell 41 measures NOx concentration in the measurement-object gas in the third internal cavity 61. The measurement pump cell 41 is an electrochemical pump cell composed of the measurement electrode 44 disposed on the upper surface of the first solid electrolyte layer 4 facing with the third internal cavity 61, the outer pump electrode 23 (the outer electrode is not limited to the outer pump electrode 23, but may be any suitable electrode outside the sensor element 101), the second solid electrolyte layer 6, the spacer layer 5, and the first solid electrolyte layer 4.

The measurement electrode 44 is a porous cermet electrode. The measurement electrode 44 functions also as a NOx reduction catalyst that reduces NOx present in the atmosphere in the third internal cavity 61.

In the measurement pump cell 41, oxygen generated by decomposition of nitrogen oxide in the atmosphere around the measurement electrode 44 is pumped out, and the amount of generated oxygen can be detected as a pump current Ip2.

To detect the oxygen partial pressure around the measurement electrode 44, the second solid electrolyte layer 6, the spacer layer 5, the first solid electrolyte layer 4, the third substrate layer 3, the measurement electrode 44, and the reference electrode 42 constitute an electrochemical sensor cell, namely an oxygen-partial-pressure detection sensor cell 82 for measurement pump control. A variable power supply 46 is controlled on the basis of an electromotive force V2 detected by the oxygen-partial-pressure detection sensor cell 82 for measurement pump control.

The measurement-object gas introduced into the second internal cavity 40 reaches the measurement electrode 44 in the third internal cavity 61 through the fourth diffusion-rate limiting part 60 under the condition that the oxygen partial pressure is controlled. Nitrogen oxide in the measurement-object gas around the measurement electrode 44 is reduced ($2NO \rightarrow N_2 + O_2$) to generate oxygen. The generated oxygen is to be pumped by the measurement pump cell 41, and at this time, a voltage Vp2 of the variable power supply 46 is controlled so that the electromotive force V2 detected by the oxygen-partial-pressure detection sensor cell 82 for measurement pump control is constant. Since the amount of oxygen generated around the measurement electrode 44 is proportional to the concentration of nitrogen oxide in the measurement-object gas, nitrogen oxide concentration in the measurement-object gas is calculated by using the pump current Ip2 in the measurement pump cell 41.

By configuring oxygen partial pressure detecting means by an electrochemical sensor cell composed of a combination of the measurement electrode 44, the first solid electrolyte layer 4, the third substrate layer 3 and the reference electrode 42, it is possible to detect an electromotive force in accordance with a difference between the amount of oxygen generated by reduction of NOx components in the atmosphere around the measurement electrode 44 and the amount of oxygen contained in the reference air, and hence it is possible to determine the concentration of NOx components in the measurement-object gas.

Also, the second solid electrolyte layer 6, the spacer layer 5, the first solid electrolyte layer 4, the third substrate layer 3, the outer pump electrode 23, and the reference electrode 42 constitute an electrochemical sensor cell 83, and it is possible to detect the oxygen partial pressure in the measurement-object gas outside the sensor by an electromotive force Vref obtained by the sensor cell 83.

In the gas sensor 100 having such a configuration, the main pump cell 21 and the auxiliary pump cell 50 are operated to supply a measurement-object gas whose oxygen partial pressure is usually kept at a low constant value (the value that does not substantially affect measurement of NOx) to the measurement pump cell 41. Therefore, NOx concentration in the measurement-object gas can be detected on the basis of the pump current Ip2 that flows as a result of pumping out of the oxygen generated by reduction of NOx by the measurement pump cell 41 and is almost in proportion to the concentration of NOx in the measurement-object gas.

The sensor element 101 further includes a heater part 70 that functions as a temperature regulator of heating and maintaining the temperature of the sensor element 101 so as to enhance the oxygen ion conductivity of the solid electrolyte. The heater part 70 includes a heater electrode 71, a heater 72, a heater lead 76, a through hole 73, a heater insulating layer 74, and a pressure relief vent 75.

The heater electrode 71 is an electrode formed in contact with the lower surface of the first substrate layer 1. The power can be supplied to the heater part 70 from the outside by connecting the heater electrode 71 with a heater power supply 77 that is an external power supply.

The heater 72 is an electrical resistor sandwiched by the second substrate layer 2 and the third substrate layer 3 from top and bottom. The heater 72 is connected with the heater electrode 71 via a heater lead 76 that connects with the heater 72 and extends in the rear end side in the longitudinal direction of the sensor element 101, and the through hole 73. The heater 72 is externally powered through the heater electrode 71 to generate heat, and heats and maintains the temperature of the solid electrolyte forming the sensor element 101.

The heater 72 is embedded over the whole area from the first internal cavity 20 to the third internal cavity 61 so that the temperature of the entire sensor element 101 can be adjusted to such a temperature that activates the solid electrolyte. The temperature may be adjusted so that the main pump cell 21, the auxiliary pump cell 50, and the measurement pump cell 41 are operable. It is not necessary that the whole area is adjusted to the same temperature, but the sensor element 101 may have temperature distribution.

In the sensor element 101 of the present embodiment, the heater 72 is embedded in the base part 102, but this form is not limitative. The heater 72 may be disposed to heat the base part 102. That is, the heater 72 may heat the sensor element 101 to develop oxygen ion conductivity with which the main pump cell 21, the auxiliary pump cell 50, and the measurement pump cell 41 are operable. For example, the heater 72 may be embedded in the base part 102 as in the present embodiment. Alternatively, for example, the heater part 70 may be formed as a heater substrate that is separate from the base part 102, and may be disposed at a position adjacent to the base part 102.

A heater insulating layer 74 is formed of an insulator such as alumina on the upper and lower surfaces of the heater 72 and the heater lead 76. The heater insulating layer 74 is formed to ensure electrical insulation between the second substrate layer 2, and the heater 72 and the heater lead 76, and electrical insulation between the third substrate layer 3, and the heater 72 and the heater lead 76.

The pressure relief vent 75 extends through the third substrate layer 3 so that the heater insulating layer 74 and the reference gas introduction space 43 communicate with each other. The pressure relief vent 75 can mitigate an increase in internal pressure due to temperature rise in the heater insulating layer 74. The pressure relief vent 75 may be absent.

(Control Unit)

The gas sensor according to the present embodiment includes the sensor element 101 described above and the control unit 90 for controlling the sensor element 101. FIG. 2 is a block diagram showing connections between the control unit 90, and the individual pump cells 21, 50, and 41 and the heater part 70 of the sensor element 101. The control unit 90 includes a heater control part 91, an activity determining part 92, a pump control part 93, an oxygen concentration detecting part 94, and a NOx concentration detecting part 95. The entity of the control unit 90 is a microprocessor designed/set to control the sensor element 101.

The control unit 90 is configured to acquire an electromotive force (V0, V1, V2, Vref) in each of the sensor cells 80, 81, 82, and 83, a pump current (Ip0, Ip1, Ip2) in each of the pump cells 21, 50, and 41, and a heater voltage Vh and a heater current Ih in the heater part 70 of the sensor element 101. Further, the control unit 90 is configured to output control signals to the variable power supplies 24, 52 and 46, and the heater power supply 77.

The heater control part 91 is configured to be able to control the temperature of the heater 72. The heater control part 91 heats the heater 72 at a desired temperature-raising-rate and maintains the temperature of the heater 72 at a desired temperature.

In order to heat the heater 72, known various control methods can be used. For example, the heater 72 may be heated by applying a certain voltage to the heater 72. The output of the heater power supply 77 may be controlled by changing it on the basis of the resistance value of the heater 72 to achieve a desired temperature-raising-rate. Alternatively, the output of the heater power supply 77 may be controlled on the basis of at least one of resistance values in the main pump cell 21, the auxiliary pump cell 50, and the measurement pump cell 41 to achieve a desired temperature-raising-rate.

For example, the heater control part 91 performs feedback control of a control signal output to the heater power supply 77 on the basis of a heater resistance value Rh (=Vh/Ih) calculated from the heater voltage Vh and the heater current Ih in the heater 72 so that the heater 72 reaches a target temperature.

The activity determining part 92 determines whether the sensor element 101 is in a measurable active state or not. Specifically, the activity determining part 92 determines whether the main pump cell 21, the auxiliary pump cell 50, and the measurement pump cell 41 are in a drivable active state or not. Here, the phrase "active state" refers to a state where the solid electrolyte constituting each of the pump cells 21, 50, and 41 has been heated by the heater 72, and as a result oxygen-ion-conductivity has been developed to the extent that pump cell control that will be described later can be performed.

Whether the sensor element 101 is in a measurable active state or not can be determined by, for example, whether oxygen-ion-conductivity has been developed to the extent that pump cell control that will be described later can be performed. When oxygen-ion-conductivity increases, a resistance value in each of the pump cells 21, 50, and 41 reduces. Whether the sensor element 101 is in an active state or not may be determined by detecting a resistance value in any one of the main pump cell 21 (the inner main pump electrode 22 and the outer pump electrode 23), the auxiliary pump cell 50 (the auxiliary pump electrode 51 and the outer pump electrode 23), and the measurement pump cell 41 (the measurement electrode 44 and the outer pump electrode 23). For example, the value of Ip0 at the time when certain Vp0 is applied to the main pump cell 21 is detected to calculate a resistance value Rp0 (=Vp0/Ip0). The sensor element 101 may be determined to be in an active state at the time when the calculated resistance value Rp0 reaches a desired value.

The resistance value Rp0 in the main pump cell 21 at which the sensor element 101 is determined to be in an active state may vary depending on the configuration of the sensor element 101. For example, the resistance value Rp0 at which the sensor element 101 is determined to be in an active state may be 300Ω to 1000Ω. Alternatively, the resistance value Rp0 at which the sensor element 101 is determined to be in an active state may be, for example, 600Ω to 1000Ω. Alternatively, the resistance value Rp0 at which the sensor element 101 is determined to be in an active state may be 300Ω to 400Ω.

As in the case of each of the pump cells 21, 50, and 41, when oxygen-ion-conductivity increases, a resistance value in each of the sensor cells 80, 81, 82, and 83 also reduces. Whether the sensor element 101 is in an active state or not may be determined by detecting a resistance value in any one of the oxygen-partial-pressure detection sensor cell 80 for main pump control (the inner main pump electrode 22 and the reference electrode 42), the oxygen-partial-pressure detection sensor cell 81 for auxiliary pump control (the auxiliary pump electrode 51 and the reference electrode 42), the oxygen-partial-pressure detection sensor cell 82 for measurement pump control (the measurement electrode 44 and the reference electrode 42), and the sensor cell 83 (the outer pump electrode 23 and the reference electrode 42).

Further, oxygen-ion-conductivity increases as the temperature of the solid electrolyte increases. In consideration of such a relationship, whether the sensor element 101 is in a measurable active state or not may be determined on the basis of the temperature of the sensor element 101 or the temperature of the heater 72.

The temperature of the heater 72 at which the sensor element 101 is determined to be in an active state may vary depending on the configuration of the sensor element 101. In the present embodiment, the temperature of the heater 72 at which the sensor element 101 is determined to be in an active state may be, for example, 550° C. to 700° C. Alternatively, the temperature of the heater 72 at which the sensor element 101 is determined to be in an active state may be, for example, 550° C. to 650° C. Alternatively, the temperature of the heater 72 at which the sensor element 101 is determined to be in an active state may be 650° C. to 700° C.

For example, when determining whether the sensor element 101 is in a measurable active state or not on the basis of the temperature of the heater 72, a correlation between the temperature of the heater 72 and oxygen-ion-conductivity in the sensor element 101 may previously be acquired to set, on the basis of the correlation, a heater temperature at which desired oxygen-ion-conductivity is developed. The sensor element 101 may be determined to be in an active state at the time when the heater 72 reaches the set temperature. The determination that a heater temperature is at the set temperature may be made using the heater resistance value Rh as in the case described above with reference to the heater control part 91.

The activity determining part 92 determines whether the sensor element 101 is in a measurable active state or not in a timely fashion while the heater control part 91 described above heats the heater 72 at a desired temperature-raising-rate. The determination in the activity determining part 92 may be made continuously or at an appropriate predetermined timing. The determination may be made using, for example, one or two or more of the resistance values in the respective pump cells 21, 50, and 41, the resistance values in the respective sensor cells 80, 81, 82, and 83, the temperature of the sensor element 101, and the temperature of the heater 72.

When the activity determining part 92 determines that the sensor element 101 has not reached a measurable active state, the heater control part 91 continues to heat the heater 72 until the sensor element 101 reaches an active state (a temperature raising step that will be described later). When the activity determining part 92 determines that the sensor element 101 has reached a measurable active state, the heater control part 91 continues to heat the heater 72, and the pump control part 93 that will be described later operates (a prior driving step that will be described later).

The temperature of the heater 72 at which the activity determining part 92 determines that the sensor element 101 is in a measurable active state is referred to as an active temperature.

The pump control part 93 controls the main pump cell 21, the auxiliary pump cell 50, and the measurement pump cell 41.

The pump control part 93 performs feedback control of the pump voltage Vp0 of the variable power supply 24 in the main pump cell 21 so that the electromotive force V0 in the oxygen-partial-pressure detection sensor cell 80 for main pump control is at a constant value (referred to as a set value $V0_{SET}$). The electromotive force V0 indicates the oxygen partial pressure in the vicinity of the inner main pump electrode 22, and therefore making the electromotive force V0 constant means that the oxygen partial pressure in the vicinity of the inner main pump electrode 22 is made constant. As a result, the pump current Ip0 in the main pump cell 21 varies depending on the oxygen concentration in the measurement-object gas.

When the oxygen partial pressure in the measurement-object gas is higher than the oxygen partial pressure corresponding to the set value $V0_{SET}$, the main pump cell 21 pumps oxygen out from the first internal space 20. On the other hand, when the oxygen partial pressure in the measurement-object gas is lower than the oxygen partial pressure corresponding to the set value $V0_{SET}$ (for example, when hydrocarbons HC or the like are contained), the main pump cell 21 pumps oxygen into the first internal space 20 from the space outside the sensor element 101. Therefore, the value of the pump current Ip0 may be either positive or negative.

The pump control part 93 performs feedback control of the pump voltage Vp1 of the variable power supply 52 in the auxiliary pump cell 50 so that the electromotive force V1 in the oxygen-partial-pressure detection sensor cell 81 for auxiliary pump control is at a constant value (referred to as a set value $V1_{SET}$). The electromotive force V1 indicates the oxygen partial pressure in the vicinity of the auxiliary pump electrode 51, and therefore making the electromotive force V1 constant means that the oxygen partial pressure in the vicinity of the auxiliary pump electrode 51 is made constant. The oxygen partial pressure in the atmosphere in the second internal space 40 is thereby controlled to be a low partial pressure that does not substantially affect measurement of NOx.

At the same time, feedback control is performed to set the set value $V0_{SET}$ of the electromotive force V0 on the basis of the pump current Ip1 in the auxiliary pump cell 50 so that the pump current Ip1 is at a constant value (referred to as a set value $Ip1_{SET}$). Specifically, the pump current Ip1 is input, as a control signal, to the oxygen-partial-pressure detection sensor cell 80 for main pump control, and the electromotive force V0 therein is controlled to be the set value $V0_{SET}$ set on the basis of the pump current Ip1 so that the oxygen partial pressure in the measurement-object gas introduced through the third diffusion-rate limiting part 30 into the second internal space 40 is controlled to have a gradient that is always constant. In use as the NOx sensor, the oxygen concentration in the second internal space 40 is maintained at a constant value of approximately 0.001 ppm by the action of the main pump cell 21 and the auxiliary pump cell 50. That is to say, the oxygen concentration in the measurement-object gas introduced through the fourth diffusion-rate limiting part 60 into the third internal space 61 is considered to be maintained at a constant value of approximately 0.001 ppm.

The pump control part 93 performs feedback control of the pump voltage Vp2 of the variable power supply 46 in the measurement pump cell 41 so that the electromotive force V2 detected in the oxygen-partial-pressure detection sensor cell 82 for measurement pump control is at a constant value (referred to as a set value $V2_{SET}$). In the measurement electrode 44, Nitrogen oxide in the measurement-object gas is reduced ($2NO \rightarrow N_2+O_2$) to generate oxygen. The generated oxygen is pumped out by the measurement pump cell 41 so that the electromotive force V2 becomes the set value $V2_{SET}$. The set value $V2_{SET}$ can be set as a value such that substantially all of NOx is decomposed at the measurement electrode 44.

The oxygen concentration detecting part 94 acquires the pump current Ip0 in the main pump cell 21 and detects the oxygen concentration in the measurement-object gas on the basis of a previously-stored correlation between the pump current Ip0 and the oxygen concentration in the measurement-object gas. A correlation between the pump current Ip0 and the oxygen concentration in the measurement-object gas corresponding to the prior driving step and that corresponding to the steady driving step may previously be stored. In the prior driving step, the oxygen concentration may be calculated on the basis of the correlation in the prior driving step, and in the steady driving step, the oxygen concentration may be calculated on the basis of the correlation in the steady driving step. Alternatively, the control unit 90 may be configured without the oxygen concentration detecting part 94.

The NOx concentration detecting part 95 acquires the pump current Ip2 in the measurement pump cell 41 and detects the NOx concentration in the measurement-object gas on the basis of a previously-stored correlation between the pump current Ip2 and the NOx concentration in the measurement-object gas. A correlation between the pump current Ip2 and the NOx concentration in the measurement-object gas corresponding to the prior driving step and that corresponding to the steady driving step may previously be stored. In the prior driving step, the NOx concentration may be calculated on the basis of the correlation in the prior driving step, and in the steady driving step, the NOx concentration may be calculated on the basis of the correlation in the steady driving step.

[Control Method of Gas Sensor]

A control method of the present invention includes:

a temperature raising step of heating the sensor element by the heater to raise a temperature of the sensor element up to an active temperature at which the activity determining part determines that the sensor element is in a measurable active state;

a prior driving step of raising the temperature of the sensor element by the heater from the active temperature up to a steady driving temperature, and operating the main pump cell and the measurement pump cell to detect NOx in the measurement-object gas; and a steady driving step of maintaining the temperature of the sensor element by the heater at the steady driving temperature, and operating the main pump cell and the measurement pump cell to continuously detect NOx in the measurement-object gas.

Figure 3:
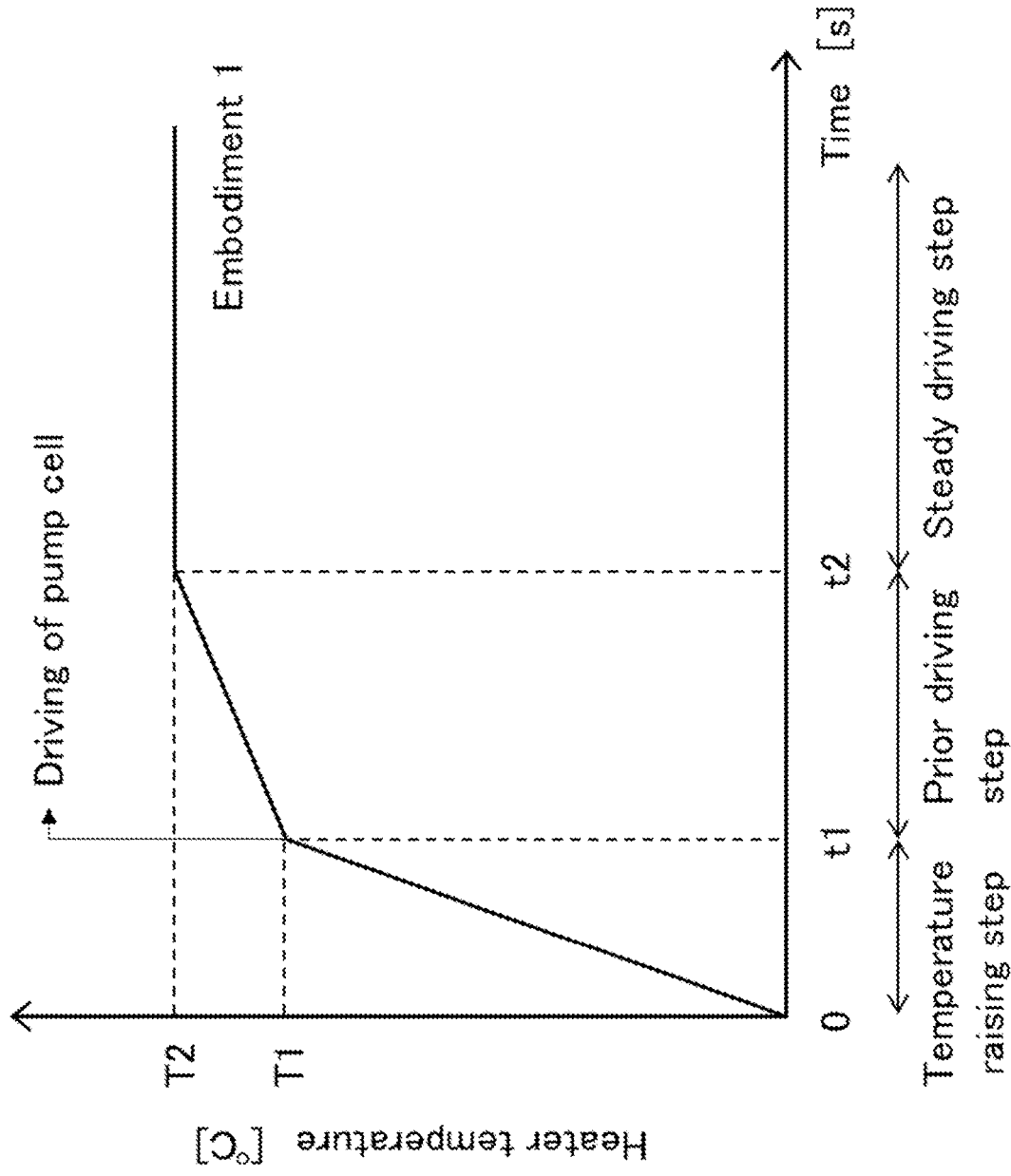
FIG. 3 is a schematic diagram showing one example of the relationship between a temporal change in heater temperature and driving of a pump cell according to Embodiment of the present invention at the time of start-up of the gas sensor 100. The horizontal axis represents time (seconds) and the vertical axis represents a heater temperature (° C.).

Control of the gas sensor 100 according to the present embodiment at the time of start-up will be described in detail below. FIG. 3 is a schematic diagram showing an example of the relationship between a temporal change in heater temperature and driving of a pump cell according to Embodiment 1 of the present invention at the time of start-up of the gas sensor 100. The horizontal axis represents time (seconds) and the vertical axis represents a heater temperature (° C.).

A method for controlling the gas sensor 100 at the time of start-up includes a temperature raising step, a prior driving step, and a steady driving step.

The time required to start accurate measurement after the start-up of the gas sensor 100 is referred to as a start-up time. The start-up time includes a heating-up time required for the heater control part 91 to raise the temperature of the sensor element 101 up to a temperature at which measurement can be performed and a time from when the pump control part 93 starts the control described above after temperature rising until when accurate measurement of a NOx concentration can be started.

In the temperature raising step, the sensor element 101 is heated by the heater 72 up to the active temperature at which the activity determining part 92 determines that the sensor element 101 is in a measurable active state.

That is, in the temperature raising step, the heater control part 91 allows the heater 72 to heat the sensor element 101 up to the active temperature at which the activity determining part 92 determines that the sensor element 101 is in a measurable active state. FIG. 3 shows that the gas sensor 100 has started-up at the origin (0 seconds) on the horizontal axis.

When the gas sensor 100 receives a start signal (Dew point), the heater control part 91 starts heating of the sensor element 101. That is to say, the temperature raising step is started. For example, when the gas sensor 100 is installed in an automobile or the like, a start signal is sent from an ECU (Electronic Control Unit) or an exhaust gas treatment system or the like to the gas sensor 100. The temperature raising step may be started by externally supplying electricity to the control unit 90 of the gas sensor 100.

When the activity determining part 92 determines that the sensor element 101 has not reached a measurable active state, the temperature raising step continues. Then, when the activity determining part 92 determines that the sensor element 101 has reached a measurable active state, the temperature raising step is completed and the prior driving step that will be described later is started.

In the temperature raising step of Embodiment 1, temperature raising is performed at a constant temperature-raising-rate for a time t1 from when the temperature raising step is started (0 seconds in FIG. 3) until when the heater 72 reaches an active temperature T1. That is to say, at the time t1, the temperature raising step is completed and the prior driving step that will be described later is started. As will be described later, in the prior driving step, NOx in a measurement-object gas can be detected. In Embodiment 1, the time t1 means the heating-up time.

The active temperature T1 may be, for example, 550° C. to 700° C. Alternatively, the active temperature T1 may be, for example, 550° C. to 650° C. Alternatively, the active temperature T1 may be 650° C. to 700° C. For example, the active temperature T1 may be 650° C. However, the active temperature T1 should be lower than a steady driving temperature T2 that will be described later.

The temperature-raising-rate at which the temperature of the heater 72 rises up to the active temperature T1 may appropriately be set so that cracks does not occur in the internal structure of the sensor element 101 during temperature rising (the probability of occurrence of cracks is low as to withstand practical use). During the temperature raising step, the temperature-raising-rate may not be constant, and the temperature-raising-rate in the temperature raising step may be set in multi stages. The number of stages or the temperature-raising-rate in each of the stages may appropriately be set.

The time t1 required to raise the temperature of the heater 72 up to the active temperature T1 (=heating-up time) may usually be, for example, 20 seconds to 50 seconds in the relation with the active temperature T1. When the time t1 is within such a range, it is possible to reduce the start-up time of the gas sensor due to a reduction in the heating-up time.

The prior driving step is started when the activity determining part 92 determines that the sensor element 101 has reached a measurable active state. That is to say, the prior driving step is started when the sensor element 101 reaches the active temperature. Then, when the sensor element 101 reaches the steady driving temperature, the prior driving step is completed and the steady driving step that will be described later is started.

In the prior driving step, the sensor element 101 is heated by the heater 72 from the active temperature up to the steady driving temperature, and the main pump cell 21 and the measurement pump cell 41 are operated to detect NOx in the measurement-object gas.

That is, in the prior driving step, the heater control part 91 allows the heater 72 to further heat the sensor element 101 from the active temperature up to a predetermined steady driving temperature previously set.

At the same time, the pump control part 93 starts to operate a pump cell including the main pump cell 21 and the measurement pump cell 41 when the sensor element 101 reaches the active temperature.

In the prior driving step of Embodiment 1, the temperature of the heater 72 rises from the active temperature T1 up to the steady driving temperature T2 at a constant temperature-raising-rate. The time that has elapsed from the start-up of the gas sensor 100 is t2. The steady driving temperature T2 may be, for example, 750° C. to 850° C. Alternatively, the steady driving temperature T2 may be, for example, 750° C. to 800° C. Alternatively, the steady driving temperature T2 may be 800° C. to 850° C.

The temperature-raising-rate in the prior driving step may appropriately be set so that cracks does not occur in the internal structure of the sensor element 101 during temperature rising (the probability of occurrence of cracks is low as to withstand practical use). During the prior driving step, the temperature-raising-rate may not be constant, and the temperature-raising-rate in the prior driving step may be set in multi stages. The number of stages or the temperature-raising-rate in each of the stages may appropriately be set.

The time of the prior driving step, that is, the time required to raise the temperature of the heater 72 from the active temperature T1 up to the steady driving temperature T2 (t2–t1) may usually be, for example, 5 seconds to 30 seconds in the relation with the active temperature T1 and the steady driving temperature T2.

Further, in the prior driving step of Embodiment 1, when the heater 72 reaches the active temperature T1, each of the pump cells 21, 50, and 41 may start to operate to detect NOx in the measurement-object gas throughout the prior driving step. Specifically, the pump control part 93 performs the various controls described above. Further, the oxygen concentration detecting part 94 and the NOx concentration detecting part 95 detect the oxygen concentration and the NOx concentration in the measurement-object gas.

The steady driving step is started when the sensor element 101 reaches the steady driving temperature. After the steady driving step is started, the steady driving step usually continues until driving of the gas sensor 100 is ended.

In the steady driving step, the sensor element 101 is maintained at the steady driving temperature by the heater 72, and the pump cell including the main pump cell 21 and the measurement pump cell 41 is operated to continuously detect NOx in the measurement-object gas.

That is, in the steady driving step, the heater control part 91 allows the heater 72 to maintain the sensor element 101 at the steady driving temperature.

At the same time, the pump control part 93 continues to operate the pump cell including the main pump cell 21 and the measurement pump cell 41 when the sensor element 101 reaches the steady driving temperature.

In the steady driving step of Embodiment 1, the heater 72 is maintained at the steady driving temperature T2.

Further, since each of the pump cells 21, 50, and 41 is continuously operated when the heater 72 reaches the steady driving temperature T2, NOx in the measurement-object gas can continuously be detected also in the steady driving step. Specifically, the pump control part 93 performs the various controls described above. Further, the oxygen concentration detecting part 94 and the NOx concentration detecting part 95 detect the oxygen concentration and the NOx concentration in the measurement-object gas.

As described above, in Embodiment 1, NOx in the measurement-object gas can be detected after the starting time t1 of the prior driving step.

As described above, the temperature at which the prior driving step is started, that is, the active temperature T1 is lower than the steady driving temperature T2. The strength of the sensor element 101 (mainly, the strength of $ZrO_2$ constituting the base part 102) increases as the temperature reduces. Therefore, the temperature-raising-rate in the temperature raising step can be increased to the extent that cracks of the internal structure of the sensor element 101 can be prevented. This makes it possible to reduce the heating-up time t1. As a result, the start-up time of the gas sensor 100 can be reduced.

Further, the shift from the prior driving step to the steady driving step makes it possible to operate each of the pump cells 21, 50, and 41 at a temperature at which oxygen-ion-conductivity is higher, thereby high detection accuracy of NOx in the measurement-object gas can be maintained as a whole.

Further, the detection accuracy of NOx in the measurement-object gas can be made higher by making the operation of each of the pump cells 21, 50, and 41 in the prior driving step different from the operation of each of the pump cells 21, 50, and 41 in the steady driving step.

Specifically, an oxygen concentration adjusted by the main pump cell 21 in the prior driving step may be made higher than an oxygen concentration adjusted by the main pump cell 21 in the steady driving step.

As described above, the temperature at which the prior driving step is started, that is, the active temperature T1 is lower than the steady driving temperature T2. The solid electrolyte constituting the base part 102 of the sensor element 101 has higher oxygen-ion-conductivity as the temperature thereof increases. The oxygen-ion-conductivity at the active temperature T1 is considered to be slightly lower than the oxygen-ion-conductivity at the steady driving temperature T2. That is to say, the resistance value Rp0 of the main pump cell 21 at the active temperature T1 is considered to be slightly higher than the resistance value Rp0 of the main pump cell 21 at the steady driving temperature T2. Therefore, particularly when the oxygen concentration in the measurement-object gas is high (i.e., when Ip0 that should flow through the main pump cell 21 is large), the pump voltage Vp0 applied to the main pump cell 21 is considered to be higher.

If the pump voltage Vp0 is too high, NOx may be decomposed in the inner main pump electrode 22. As a result, the current value Ip2 detected by the measurement pump cell 41 may be smaller than a value that is to be originally detected. Therefore, particularly when the oxygen concentration in the measurement-object gas is high, NOx detection accuracy may reduce.

When the oxygen concentration adjusted by the main pump cell 21 in the prior driving step is made higher than the oxygen concentration adjusted by the main pump cell 21 in the steady driving step, Ip0 that should flow through the main pump cell 21 depending on the oxygen concentration in the measurement-object gas can be reduced. This makes it possible to suppress increase of the pump voltage Vp0 particularly when the oxygen concentration in the measurement-object gas is high. Therefore, it is possible to further increase the detection accuracy of NOx in the measurement-object gas.

Further, the electromotive force V1 between the auxiliary pump electrode 51 and the reference electrode 42 in the prior driving step may be controlled to be a smaller value than the electromotive force V1 between the auxiliary pump electrode 51 and the reference electrode 42 in the steady driving step.

That is to say, in the prior driving step, the set value $V1_{SET}$ of the electromotive force V1 in the oxygen-partial-pressure detection sensor cell 81 for auxiliary pump control may be set to a smaller value than the set value $V1_{SET}$ in the steady driving step. The set value (set value at the steady driving temperature T2) $V1_{SET}$ in the steady driving step may be 350 mV to 430 mV.

The set value $V1_{SET}$ at the start of the prior driving step, that is, at the active temperature T1 may be 300 mV to 380 mV. However, the set value $V1_{SET}$ at the active temperature T1 should be smaller than the value of the set value $V1_{SET}$ in the steady driving step.

In the prior driving step, the set value $V1_{SET}$ may be changed continuously or stepwise from the set value $V1_{SET}$ at the active temperature T1 to the set value $V1_{SET}$ at the steady driving temperature T2. Alternatively, the set value $V1_{SET}$ at the active temperature T1 may always be used during the prior driving step.

Alternatively, the pump current Ip1 flowing through the auxiliary pump cell 50 in the prior driving step may be controlled to be a larger value than the pump current Ip1 flowing through the auxiliary pump cell 50 in the steady driving step.

That is to say, in the prior driving step, the set value $Ip1_{SET}$ of the pump current Ip1 in the auxiliary pump cell 50 may be set to a larger value than the set value $Ip1_{SET}$ in the steady driving step. The set value $Ip1_{SET}$ in the steady driving step may be 3 μA to 10 μA.

The set value $Ip1_{SET}$ at the start of the prior driving step, that is, at the active temperature T1 may be 5 μA to 15 μA.

However, the set value $Ip1_{SET}$ at the active temperature T1 should be larger than the value of the set value $Ip1_{SET}$ in the steady driving step.

In the prior driving step, the set value $Ip1_{SET}$ may be changed continuously or stepwise from the set value $Ip1_{SET}$ at the active temperature T1 to the set value $Ip1_{SET}$ at the steady driving temperature T2. Alternatively, the set value $V1_{SET}$ at the active temperature T1 may always be used during the prior driving step.

Performing such control based on the set value $V1_{SET}$ and/or the set value $Ip1_{SET}$ results in making the oxygen concentration adjusted by the main pump cell 21 in the prior driving step higher than the oxygen concentration adjusted by the main pump cell 21 in the steady driving step.

As described above, when the oxygen concentration adjusted by the main pump cell 21 in the prior driving step is made higher than the oxygen concentration adjusted by the main pump cell 21 in the steady driving step, Ip0 that should flow through the main pump cell 21 depending on the oxygen concentration in the measurement-object gas can be reduced. As a result, it is possible to suppress increase of the pump voltage Vp0 particularly when the oxygen concentration in the measurement-object gas is high. Therefore, it is possible to further increase the detection accuracy of NOx in the measurement-object gas.

Further, the oxygen concentration adjusted by the main pump cell 21 in the steady driving step is sufficiently low, and therefore it is considered that degradation of the measurement electrode 44 can further be reduced in the case of long-term use. When the oxygen concentration near the measurement electrode 44 is sufficiently low, it is considered that oxidation or evaporation of metal components of the measurement electrode 44 can be suppressed. Therefore, it is possible to prevent a reduction (degradation) in the catalytic activity of the measurement electrode 44 to reduce (decompose) NOx. As a result, it is possible to maintain high detection accuracy even in the case of long-term use.

Further, in the prior driving step, the electromotive force V2 between the measurement electrode 44 and the reference electrode 42 in the oxygen-partial-pressure detection sensor cell 82 for measurement pump control may be controlled to be a different value from the electromotive force V2 between the measurement electrode 44 and the reference electrode 42 in the steady driving step. Preferably, the electromotive force V2 between the measurement electrode 44 and the reference electrode 42 in the prior driving step may be controlled to be a larger value than the electromotive force V2 between the measurement electrode 44 and the reference electrode 42 in the steady driving step.

Before the start of the prior driving step (before t1 in FIG. 3), the inside of the measurement-object gas flow part 15 is filled with a gas atmosphere (e.g., with an air atmosphere) around the gas sensor 100. Therefore, before the start of the prior driving step, the concentration of oxygen in the third internal space 61 is usually higher than that when the prior driving step is performed. That is to say, the vicinity of the measurement electrode 44 is in a state where a larger amount of oxygen is present than when the prior driving step is performed.

When the prior driving step is started in such a state, immediately after the start of the prior driving step, the measurement pump cell 41 pumps out oxygen having existed in the third internal space 61 before the start of the prior driving step, in addition to oxygen derived from NOx in the measurement-object gas. Therefore, immediately after the start of the prior driving step, the pump current Ip2 flowing through the measurement pump cell 41 may have a larger current value than a current value corresponding to the NOx concentration in the measurement-object gas. As a result, immediately after the start of the prior driving step, there is a case where a NOx concentration calculated on the basis of the pump current Ip2, that is, the NOx concentration output value of the gas sensor 100 is output as a larger value than the actual NOx concentration in the measurement-object gas.

In order to quickly pump out oxygen having existed in the third internal space 61 before the start of the prior driving step by the measurement pump cell 41, the electromotive force V2 between the measurement electrode 44 and the reference electrode 42 in the prior driving step may be controlled to be a different value from the electromotive force V2 between the measurement electrode 44 and the reference electrode 42 in the measurement pump cell 41 in the steady driving step. Preferably, the electromotive force V2 between the measurement electrode 44 and the reference electrode 42 in the prior driving step may be controlled to be a larger value than the electromotive force V2 between the measurement electrode 44 and the reference electrode 42 in the measurement pump cell 41 in the steady driving step.

That is to say, in the prior driving step, the set value $V2_{SET}$ of the electromotive force V2 in the oxygen-partial-pressure detection sensor cell 82 for measurement pump control may be set to a larger value than the set value $V2_{SET}$ in the steady driving step. The set value (set value at the steady driving temperature T2) $V2_{SET}$ in the steady driving step may be 350 mV to 550 mV.

The set value $V2_{SET}$ at the start of the prior driving step, that is, at the active temperature T1 may be 400 mV to 1.2 V. However, the set value $V2_{SET}$ at the active temperature T1 should be different from the value of the set value $V2_{SET}$ in the steady driving step. More preferably, the set value $V2_{SET}$ at the active temperature T1 should be larger than the set value $V2_{SET}$ in the steady driving step.

In the prior driving step, the set value $V2_{SET}$ may be changed continuously or stepwise from the set value $V2_{SET}$ at the active temperature T1 to the set value $V2_{SET}$ at the steady driving temperature T2. Alternatively, the set value $V2_{SET}$ at the active temperature T1 may always be used during the prior driving step.

Performing such control based on the set value $V2_{SET}$ makes it possible to quickly pump out oxygen having existed in the third internal space 61 before the start of the prior driving step in the measurement pump cell 41. As a result, it is possible to detect only oxygen derived from NOx in the measurement-object gas as the pump current Ip2 in the measurement pump cell 41 from an earlier stage after the start of the prior driving step. Therefore, the gas sensor 100 can accurately detect a NOx concentration from an earlier stage after the start of the prior driving step. That is to say, it is possible to further reduce the time until accurate measurement of a NOx concentration can be started after temperature rising of the sensor element 101.

In the prior driving step, the heater 72 may be heated from the active temperature T1 up to the steady driving temperature T2 on the basis of a predetermined temperature-raising-rate.

In Embodiment 1 described above, as shown in FIG. 3, the temperature-raising-rate of the heater 72 is constant throughout the prior driving step. As described above, the temperature-raising-rate does not need to be constant and may be set in multi stages in the prior driving step. The number of stages or the temperature-raising-rate in each of the stages may appropriately be set.

Figure 4:
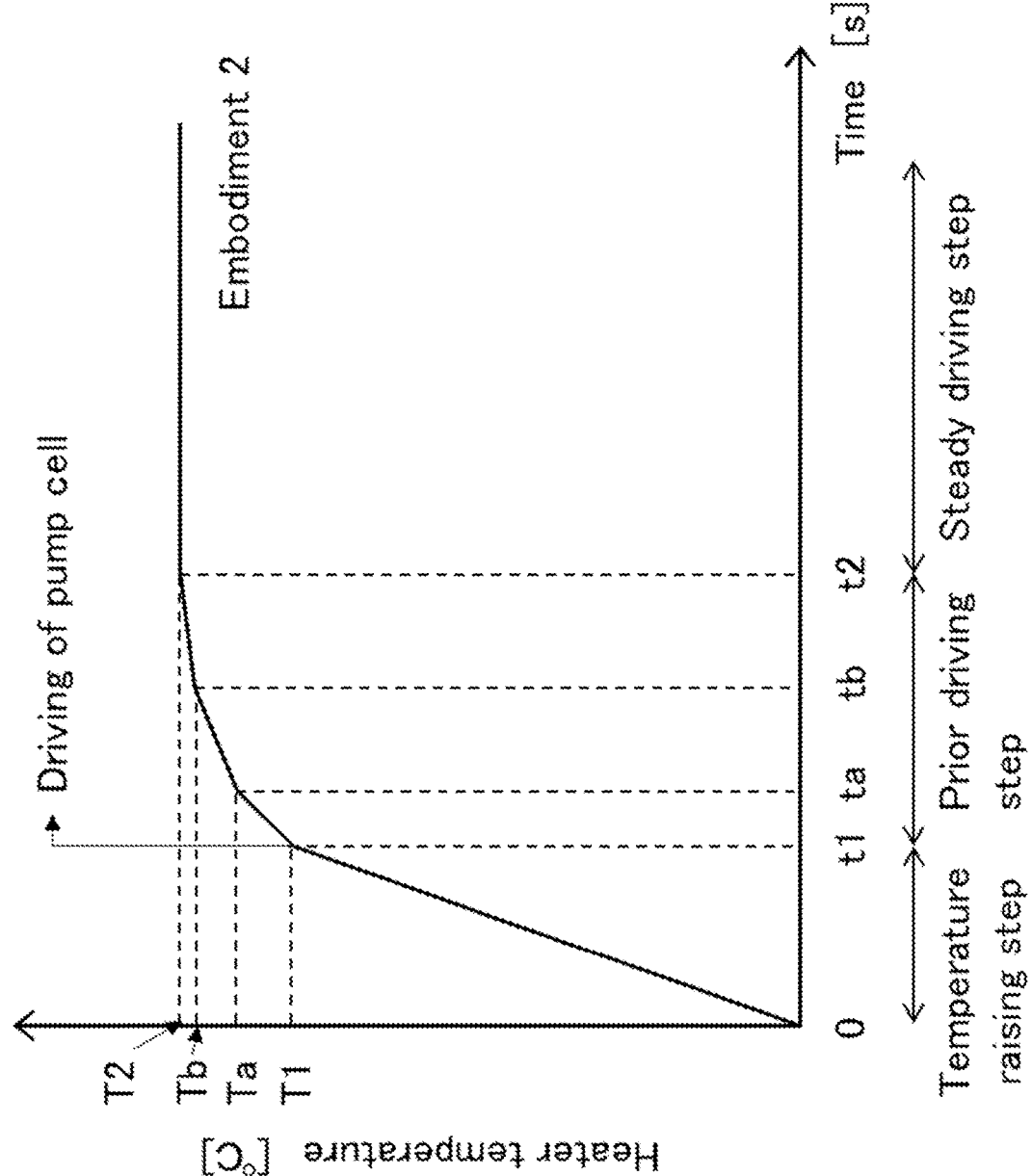
FIG. 4 is a schematic diagram showing another example of the relationship between a temporal change in heater temperature and driving of a pump cell according to Embodiment of the present invention at the time of start-up of the gas sensor 100. The horizontal axis represents time (seconds) and the vertical axis represents a heater temperature (° C.).

For example, FIG. 4 shows, as Embodiment 2, a case where the temperature-raising-rate is set in three stages in the prior driving step. FIG. 4 is a schematic diagram showing the relationship between a temporal change in heater temperature and driving of a pump cell according to Embodiment 2 at the time of start-up of the gas sensor 100. The horizontal axis represents time (seconds) and the vertical axis represents a heater temperature (° C.). Also in FIG. 4, similarly to FIG. 3, the starting time of the temperature raising step is set to 0 seconds.

In Embodiment 2, the temperature rising process of the heater 72 in the prior driving step is divided into three stages. Referring to FIG. 4, the first stage of temperature rising in the prior driving step starts from an active temperature T1 (time t1) at which the temperature raising step is completed, and the temperature is raised up to a temperature Ta (time ta) at a constant temperature-raising-rate. The second stage of temperature rising in the prior driving step starts from the temperature Ta (time ta), and the temperature is raised up to a temperature Tb (time tb) at a constant temperature-raising-rate. The third stage of temperature rising in the prior driving step starts from the temperature Tb (time tb), and the temperature is raised up to a steady driving temperature T2 (time t2) at a constant temperature-raising-rate.

In the prior driving step of Embodiment 2, the temperature-raising-rate is switched in three stages so that the individual stages are continuous with each other. As shown in FIG. 4, the temperature of the heater 72 is preferably raised so that the temperature-raising-rate in each of the stages becomes smaller in the order of the first stage, the second stage, and the third stage. Such temperature raising makes it possible to further reduce the temperature-raising-rate in a state where the strength of the sensor element 101 is reduced due to high temperature. Therefore, it is possible to further reduce the risk of occurrence of cracks in the internal structure of the sensor element 101.

Comparative Embodiments 1 and 2

Figure 5:
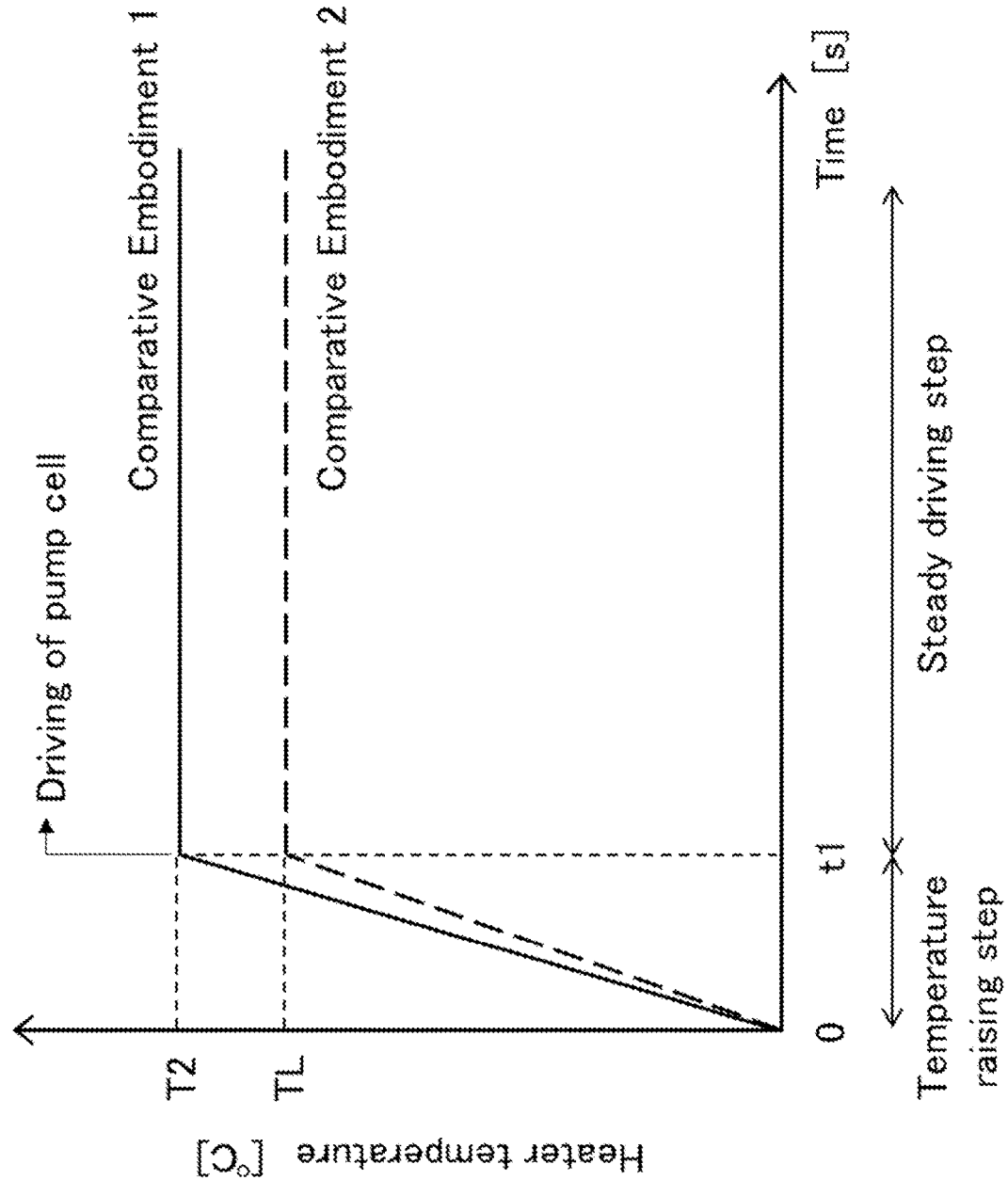
FIG. 5 is a schematic diagram showing examples of the relationship between a temporal change in heater temperature and a driving step according to Comparative Embodiments at the time of start-up of the gas sensor 100. The horizontal axis represents time (seconds) and the vertical axis represents a heater temperature (° C.).

FIG. 5 is a schematic diagram showing examples of the relationship between a temporal change in heater temperature and a driving step according to Comparative Embodiments 1 and 2 at the time of start-up of the gas sensor 100. The horizontal axis represents time (seconds) and the vertical axis represents a heater temperature (° C.). Also in FIG. 5, similarly to FIG. 3, the starting time of the temperature raising step is set to 0 seconds.

Comparative Embodiment 1 is an embodiment in which the heating-up time is reduced to t1 by raising the temperature of the heater 72 up to the steady driving temperature T2 at a high temperature-raising-rate. In such an embodiment, the heating-up time itself can be reduced.

However, when the temperature of the heater 72 is raised to the steady driving temperature T2 at a high temperature-raising-rate, there is a problem of an increased risk of the occurrence of cracking in the internal structure of the sensor element 101.

Specifically, in Comparative Embodiment 1, the sensor element 101 is heated by the heater 72 internally embedded. If the temperature-raising-rate of the heater 72 is too high, there is a problem that a temperature difference is caused between the heater 72 and an area of the sensor element 101 far from the heater 72 in the process of temperature rising so that cracking occurs in the internal structure of the sensor element 101. Particularly when the temperature of the sensor element 101 is high, there is a problem that cracking is more likely to occur in the internal structure of the sensor element 101 due to a reduction in the strength of the solid electrolyte (e.g., $ZrO_2$) constituting the sensor element 101.

Comparative Embodiment 2 is an embodiment in which the heating-up time is reduced to t1 by raising the temperature of the heater 72 up to a temperature TL set as a lower value than the active temperature T1 in Embodiments 1 and 2 and performing steady driving from the temperature TL. Since the temperature TL is lower than a conventional steady driving temperature T2, the heating-up time can be reduced even when temperature raising is performed at a conventional temperature-raising-rate.

However, the temperature TL is lower than the active temperature T1 in Embodiments 1 and 2. Therefore, the oxygen-ion-conductivity of the solid electrolyte constituting the base part 102 at the temperature TL is lower than oxygen-ion-conductivity at the active temperature T1. Therefore, the resistance value Rp0 in the main pump cell 21 is considered to be larger. When the resistance value Rp0 in the main pump cell 21 is high, the value of the pump voltage Vp0 applied in the main pump cell 21 when the oxygen concentration in the measurement-object gas is adjusted is considered to increase. Particularly when the oxygen concentration in the measurement-object gas is high, the pump voltage Vp0 further increases. In this case, particularly when the oxygen concentration in the measurement-object gas is high, part of NOx is decomposed in the inner main pump electrode 22 constituting the main pump cell 21. As a result, the current value Ip2 detected by the measurement pump cell 41 becomes smaller than a value that should really be detected. Therefore, particularly when the oxygen concentration in the measurement-object gas is high, there is a problem that the detection accuracy of NOx in the measurement-object gas reduces.

When the gas sensor 100 is used for a long time, the resistance value Rp0 of the main pump cell 21 usually tends to increase. In Comparative Embodiment 2, as described above, the value of the pump voltage Vp0 in the main pump cell 21 is large. Therefore, in the case of Comparative Embodiment 2, when the gas sensor 100 is used for a long time, there is a fear that the detection accuracy of NOx in the measurement-object gas further reduces.

Hereinafter, the case of actually manufacturing a gas sensor is described as Examples. The present invention is not limited to the following Examples.

Example 1

As Example 1, the gas sensor 100 shown in FIG. 1 and FIG. 2 was manufactured. Specifically, the sensor element 101 was produced in the following manner. First, zirconia particles containing 4 mol % of yttria as a stabilizer, an organic binder, a dispersant, a plasticizer, and an organic solvent were mixed, and six ceramics green sheets corresponding to the respective layers 1 to 6 were formed by tape casting. Then, the ceramics green sheets corresponding to the respective layers 1 to 6 were subjected to processing for forming holes such as sheet holes used for positioning at the time of printing or stacking and the internal spaces 20, 40, and 61, and various patterns for forming an electrode etc. were formed on each of the layers by screen printing. Then, the green sheets corresponding to the respective layers 1 to 6 were stacked and contact-bonded to obtain a laminated body. The obtained laminated body was cut into units of sensor elements 101. The cut laminated body was fired to obtain a sensor element 101. The thus produced sensor element 101 was electrically connected to each of the power supplies and the control unit 90 to produce the gas sensor 100 of Example 1.

In the gas sensor 100 of Example 1, the set value $V1_{SET}$, the set value $Ip1_{SET}$, and the set value $V2_{SET}$ in the prior driving step and the set value $V1_{SET}$, the set value $Ip1_{SET}$, and the set value $V2_{SET}$ in the steady driving step were set to respective values shown in Table 1.

Examples 2 to 3

In the gas sensor 100 of Examples 2 and 3, the set values $V1_{SET}$, the set values $Ip1_{SET}$, and the set values $V2_{SET}$ in the prior driving step and the set values $V1_{SET}$, the set values $Ip1_{SET}$, and the set values $V2_{SET}$ in the steady driving step were set to respective values shown in Table 1. Except for the above, the gas sensor 100 of Examples 2 and 3 was prepared in the same manner as for the gas sensor 100 of Example 1.

Comparative Example 1

A gas sensor 100 was produced in the same manner as in Example 1 except that the prior driving step was not performed. The set value $V1_{SET}$, the set value $Ip1_{SET}$, and the set value $V2_{SET}$ in the steady driving step were set to respective values shown in Table 1.

Figure 6:
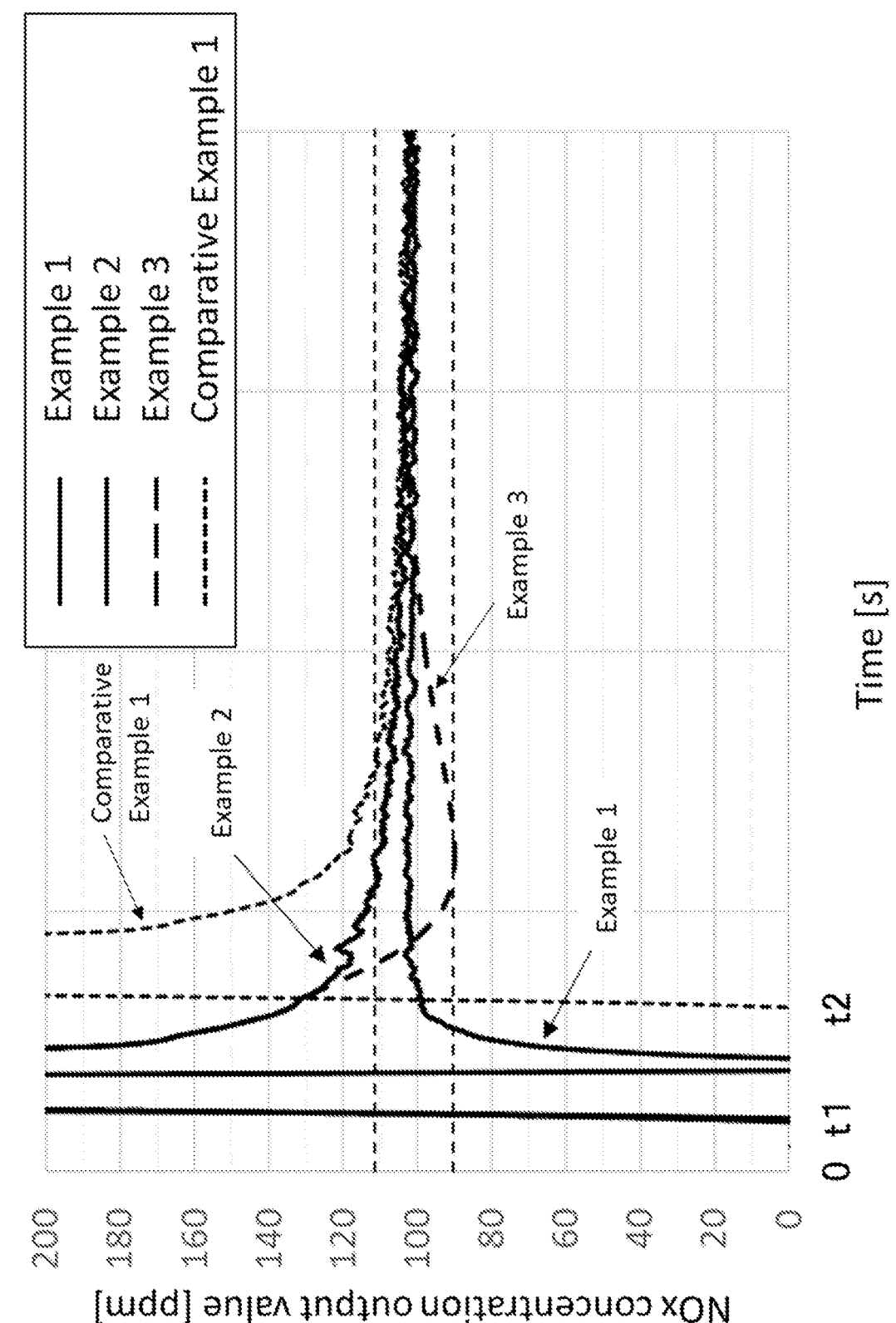
FIG. 6 is a diagram showing a temporal change in NOx concentration output value at the time of start-up of each of the gas sensors 100 of Examples 1 to 3 and Comparative Example 1. The horizontal axis represents time (seconds) and the vertical axis represents the NOx concentration output value (ppm) of the gas sensor 100.

FIG. 6 shows a temporal change in NOx concentration output value at the time of start-up of each of the gas sensors 100 of Examples 1 to 3 and Comparative Example 1. The horizontal axis represents time (seconds) and the vertical axis represents the NOx concentration output value (ppm) of the gas sensor 100. Also in FIG. 6, similarly to FIG. 3, the starting time of the temperature raising step is set to 0 seconds. The time from when the gas sensor 100 started up until when the NOx concentration output value fell within 100 ppm±10 ppm (90 ppm to 110 ppm) was defined as a start-up time.

In all of Examples 1 to 3, the start-up time was confirmed to be obviously shorter than that in the case of Comparative Example 1.

In Example 3, the set value $V1_{SET}$ and the set value $Ip1_{SET}$ in the prior driving step were the same as the set value $V1_{SET}$ and the set value $Ip1_{SET}$ in the steady driving step. On the other hand, in Examples 1 and 2, the set value $V1_{SET}$ in the prior driving step was set to be smaller than the set value $V1_{SET}$ in the steady driving step, and the set value $Ip1_{SET}$ in the prior driving step was set to be larger than the set value $Ip1_{SET}$ in the steady driving step. That is to say, the oxygen concentration in the first internal space 20 adjusted by the main pump cell 21 in the prior driving step was controlled to be higher than the oxygen concentration in the first internal space 20 in the steady driving step.

TABLE 1

| | Prior driving | Set values in prior driving step | | | Set values in steady driving step | | |
|---|---|---|---|---|---|---|---|
| | step | $V1_{SET}$ | $Ip1_{SET}$ | $V2_{SET}$ | $V1_{SET}$ | $Ip1_{SET}$ | $V2_{SET}$ |
| Example 1 | Yes | 340 mV | 10 μA | 600 mV | 385 mV | 7 μA | 400 mV |
| Example 2 | Yes | 340 mV | 10 μA | 400 mV | 385 mV | 7 μA | 400 mV |
| Example 3 | Yes | 385 mV | 7 μA | 400 mV | 385 mV | 7 μA | 400 mV |
| Comparative Example 1 | No | — | — | — | 385 mV | 7 μA | 400 mV |

In all of Examples 1 to 3 and Comparative Example 1, the heater control part 91 was configured so as to perform such temperature raising as shown in FIG. 3. The active temperature T1 was set to 600° C., and the steady driving temperature T2 was set to 800° C. That is to say, in all of Examples 1 to 3 and Comparative Example 1, the temperature of the heater 72 was raised in the same manner.

In all of Examples 1 to 3, the gas sensor 100 was configured so that the prior driving step was started when the temperature of the heater 72 reached 600° C.

[Measurement of Start-Up Time]

The start-up time of each of the produced gas sensors of Examples 1 to 3 and Comparative Example 1 was measured. Specifically, the measurement was performed in the following manner.

Each of the gas sensors of Examples 1 to 3 and Comparative Example 1 was measured in a model gas device. Each of the gas sensors of Examples 1 to 3 and Comparative Example 1 was connected to a piping for measurement of the model gas device. A model gas satisfying NO=500 ppm and $O2=18\%$ was flowed through the piping for measurement, and in such a state, each of the gas sensors of Examples 1 to 3 and Comparative Example 1 was driven to measure the wave form of a NOx concentration output value. It is to be noted that gas components other than NO and $O_2$ in the model gas used for measurement were $H_2O$ (3%) and $N_2$ (remainder). The units of the gas components were all on the basis of volume.

In Examples 1 and 2, a slow change in NOx concentration output value from about 90 ppm to a real concentration of 100 ppm was not observed unlike Example 3. In Examples 1 and 2, the oxygen concentration in the first internal space 20 in the prior driving step was controlled to be higher than that in the steady driving step, and therefore the pump current Ip0 that should flow through the main pump cell 21 depending on the oxygen concentration in the measurement-object gas was considered to be smaller than that in the case of Example 3. It was estimated that this made it possible to prevent the pump voltage Vp0 from becoming too high. As a result, in Examples 1 and 2, the NOx concentration output value calculated from the value of the current Ip2 flowing through the measurement pump cell 41 was considered to more quickly come to show the NOx concentration in the measurement-object correctly.

In Example 1, further, the set value $V2_{SET}$ in the prior driving step was set to be larger than the set value $V2_{SET}$ in the steady driving step. As a result, in the measurement pump cell 41, oxygen having existed in the third internal space 61 before the start of the prior driving step could more quickly be pumped out, which was considered to further reduce the start-up time.

According to the present invention, it is possible to reduce the heating-up time of the sensor element 101 while solving the above-described problems of Comparative Embodiments 1 and 2. As a result, the start-up time of the gas sensor 100 can be reduced.

Therefore, according to the present invention, the gas sensor can be controlled to detect NOx in the measurement-object gas so that the start-up time from when the gas sensor starts up until when accurate measurement can be started is reduced.

Further, according to the present invention, the gas sensor can be controlled to detect NOx in the measurement-object gas so that a short start-up time from when the gas sensor starts up until when accurate measurement can be started is achieved and high NOx detection accuracy of the gas sensor is maintained during long-term use even when the oxygen concentration in the measurement-object gas is high.

What is claimed is:

1. A control method of a gas sensor for detecting NOx in a measurement-object gas, the gas sensor comprising:
   a sensor element, and
   an activity determining part for determining whether the sensor element is in a measurable active state or not, wherein
   the sensor element comprises:
      a base part in an elongated plate shape, including a plurality of oxygen-ion-conductive solid electrolyte layers stacked;
      a measurement-object gas flow part for introduction and flow of the measurement-object gas through one end part in a longitudinal direction of the base part;
      a main pump cell for adjusting an oxygen concentration in the measurement-object gas to a desired concentration, the main pump cell including:
   an inner main pump electrode disposed on an inner surface of the measurement-object gas flow part; and an outer pump electrode disposed at a position different from the measurement-object gas flow part on the base part and corresponding to the inner main pump electrode;
      a measurement pump cell for detecting NOx in the measurement-object gas, the measurement pump cell including: a measurement electrode disposed at a position farther from the one end part in the longitudinal direction of the base part than the inner main pump electrode on the inner surface of the measurement-object gas flow part; and an outer pump electrode disposed at a position different from the measurement-object gas flow part on the base part and corresponding to the measurement electrode;
      a heater for heating the base part; and
      a reference electrode disposed inside the base part to be in contact with a reference gas, and
   the control method comprising:
      a temperature raising step of heating the sensor element by the heater to raise a temperature of the sensor element up to an active temperature at which the activity determining part determines that the sensor element is in a measurable active state;
      a prior driving step of raising the temperature of the sensor element by the heater from the active temperature up to a steady driving temperature, and operating the main pump cell and the measurement pump cell to detect NOx in the measurement-object gas; and
      a steady driving step of maintaining the temperature of the sensor element by the heater at the steady driving temperature, and operating the main pump cell and the measurement pump cell to continuously detect NOx in the measurement-object gas, and wherein
   an oxygen concentration in the measurement-object gas flow part adjusted by the main pump cell in the prior driving step is higher than an oxygen concentration in the measurement-object gas flow part adjusted by the main pump cell in the steady driving step.

2. The control method according to claim 1, wherein the sensor element further comprises:
   an auxiliary pump cell including an auxiliary pump electrode disposed at a position farther from the one end part in the longitudinal direction of the base part than the inner main pump electrode on the inner surface of the measurement-object gas flow part, and an outer pump electrode disposed at a position different from the measurement-object gas flow part on the base part and corresponding to the auxiliary pump electrode,
   wherein the auxiliary pump electrode is disposed at a position closer to the one end part in the longitudinal direction of the base part than the measurement electrode.

3. The control method according to claim 2, wherein,
   in the auxiliary pump cell, a pump current flowing through the auxiliary pump cell is controlled based on an electromotive force between the auxiliary pump electrode and the reference electrode; and
   in the main pump cell, an electromotive force between the inner main pump electrode and the reference electrode is controlled so that the pump current flowing through the auxiliary pump cell is at a constant value.

4. The control method according to claim 3, wherein, in the prior driving step, an electromotive force between the auxiliary pump electrode and the reference electrode is controlled to a smaller value than an electromotive force between the auxiliary pump electrode and the reference electrode in the steady driving step.

5. The control method according to claim 3, wherein, in the prior driving step, a pump current flowing through the auxiliary pump cell is controlled to a larger value than a pump current flowing through the auxiliary pump cell in the steady driving step.

6. The control method according to claim 1, wherein, in the measurement pump cell, a pump current flowing through the measurement pump cell is controlled based on an electromotive force between the measurement electrode and the reference electrode; and
   in the prior driving step, an electromotive force between the measurement electrode and the reference electrode is controlled to a different value from an electromotive force between the measurement electrode and the reference electrode in the steady driving step.

7. The control method according to claim 6, wherein, in the prior driving step, the electromotive force between the measurement electrode and the reference electrode is controlled to a larger value than the electromotive force between the measurement electrode and the reference electrode in the steady driving step.

8. The control method according to claim 1, wherein the activity determining part determines whether the sensor element is in the measurable active state or not, based on at least one selected from the group consisting of a temperature of the heater, a resistance value of the main pump cell, and a resistance value between the inner main pump electrode and the reference electrode.

9. The control method according to claim 1, wherein, in the prior driving step, the heater is heated from the active temperature up to the steady driving temperature based on a predetermined temperature-raising-rate in the prior driving step.

10. The control method according to claim 9, wherein the temperature-raising-rate in the prior driving step is set in multi stages.

11. The control method according to claim 1, wherein, in the temperature raising step, the heater is heated up to the active temperature based on a predetermined temperature-raising-rate in the temperature raising step.

12. The control method according to claim 11, wherein the temperature-raising-rate in the temperature raising step is set in multi stages.

13. A gas sensor comprising a sensor element and a control unit for controlling the sensor element, wherein the sensor element comprises:

a base part in an elongated plate shape, including a plurality of oxygen-ion-conductive solid electrolyte layers stacked;

a measurement-object gas flow part for introduction and flow of a measurement-object gas through one end part in a longitudinal direction of the base part;

a main pump cell for adjusting an oxygen concentration in the measurement-object gas to a desired concentration, the main pump cell including:

an inner main pump electrode disposed on an inner surface of the measurement- object gas flow part; and an outer pump electrode disposed at a position different from the measurement-object gas flow part on the base part and corresponding to the inner main pump electrode;

a measurement pump cell for detecting NOx in the measurement-object gas, the measurement pump cell including: a measurement electrode disposed at a position farther from the one end part in the longitudinal direction of the base part than the inner main pump electrode on the inner surface of the measurement-object gas flow part; and an outer pump electrode disposed at a position different from the measurement-object gas flow part on the base part and corresponding to the measurement electrode;

a heater for heating the base part; and a reference electrode disposed inside the base part to be in contact with a reference gas, and the control unit comprises:

an activity determining part for determining whether the sensor element is in a measurable active state or not;

a heater control part for controlling a temperature of the heater; and a pump control part for operating the main pump cell and the measurement pump cell to detect NOx in the measurement-object gas, wherein the activity determining part determines whether the sensor element is in the measurable active state or not; the heater control part heats the sensor element by the heater up to an active temperature at which the activity determining part determines that the sensor element is the measurable active state, and further heats the sensor element up to a steady driving temperature; and the pump control part starts to operate the main pump cell and the measurement pump cell when the sensor element reaches the active temperature, and further continues to operate the main pump cell and the measurement pump cell when the sensor element reaches the steady driving temperature, and wherein an oxygen concentration in the measurement-object gas flow part adjusted by the main pump cell when the sensor element reaches the active temperature is higher than an oxygen concentration in the measurement-object gas flow part adjusted by the main pump cell when the sensor element reaches the steady driving temperature.

* * * * *